United States Patent
Xu et al.

(10) Patent No.: US 10,335,038 B2
(45) Date of Patent: Jul. 2, 2019

(54) SPECTRAL UNMIXING FOR IN-VIVO IMAGING

(75) Inventors: Heng Xu, Alameda, CA (US); Bradley W. Rice, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 3704 days.

(21) Appl. No.: 11/844,920

(22) Filed: Aug. 24, 2007

(65) Prior Publication Data
US 2008/0051665 A1 Feb. 28, 2008

Related U.S. Application Data

(60) Provisional application No. 60/840,247, filed on Aug. 24, 2006.

(51) Int. Cl.
*G01N 21/64* (2006.01)
*G01N 21/25* (2006.01)
*A61B 5/00* (2006.01)

(52) U.S. Cl.
CPC ....... *A61B 5/0059* (2013.01); *G01N 21/6428* (2013.01); *G01N 21/6456* (2013.01); *A61B 2503/40* (2013.01)

(58) Field of Classification Search
USPC ............... 600/407, 476; 250/363.01, 317
See application file for complete search history.

(56) References Cited

U.S. PATENT DOCUMENTS

| | | | |
|---|---|---|---|
| 5,205,291 A * | 4/1993 | Potter | 600/431 |
| 5,865,754 A * | 2/1999 | Sevick-Muraca et al. | 600/476 |
| 5,943,129 A | 8/1999 | Hoyt et al. | |
| 6,373,568 B1 | 4/2002 | Miller et al. | |
| 6,403,947 B1 | 6/2002 | Hoyt et al. | |
| 6,615,063 B1 * | 9/2003 | Ntziachristos et al. | 600/312 |
| 6,665,072 B2 | 12/2003 | Hoyt | |
| 6,687,620 B1 * | 2/2004 | Haaland | G01N 21/274 702/22 |
| 6,690,466 B2 | 2/2004 | Miller et al. | |
| 6,693,710 B1 | 2/2004 | Hoyt | |
| 6,750,964 B2 | 6/2004 | Levenson et al. | |
| 6,924,893 B2 | 8/2005 | Oldenbourg et al. | |
| 7,113,217 B2 * | 9/2006 | Nilson et al. | 348/373 |
| 7,298,415 B2 | 11/2007 | Nilson et al. | |

(Continued)

OTHER PUBLICATIONS

Chorvat, Jr. et al., "Spectral Unmixing of Flavin Autofluorescence Components in Cardiac Myocytes," received Sep. 2, 2005 for editing; published in Biophysical Journal: Biophysical Letters, 2005, pp. L55-L57.

(Continued)

*Primary Examiner* — Patricia J Park
(74) *Attorney, Agent, or Firm* — Fish & Richardson P.C.

(57) ABSTRACT

Described herein are systems and methods for spectral unmixing of in vivo light data. The spectral unmixing separates image data according to spectra from multiple internal light sources in an effort to isolate one or more spectrum of interest. The spectral unmixing obtains images with a combination of different and known excitation and emission limits. The spectral unmixing then uses an iterative solution process to separate spectra for the multiple fluorescent light sources, and provides a spectrum and/or a spatial distribution map for at least one of the internal light sources.

31 Claims, 14 Drawing Sheets

(56) References Cited

U.S. PATENT DOCUMENTS

| | | |
|---|---|---|
| 2003/0002028 A1 | 1/2003 | Rice |
| 2004/0027659 A1 | 2/2004 | Messerschmidt |
| 2005/0065440 A1 | 3/2005 | Levenson |
| 2005/0237423 A1 | 10/2005 | Nilson et al. |
| 2006/0118742 A1 | 6/2006 | Levenson |
| 2006/0119865 A1 | 6/2006 | Hoyt |
| 2006/0146346 A1* | 7/2006 | Hoyt ............................ 356/625 |
| 2006/0203244 A1 | 9/2006 | Nilson et al. |
| 2006/0245631 A1 | 11/2006 | Levenson |
| 2007/0016078 A1 | 1/2007 | Hoyt |
| 2007/0016082 A1 | 1/2007 | Levenson et al. |
| 2007/0253908 A1 | 11/2007 | Rice et al. |
| 2008/0294032 A1* | 11/2008 | Levenson et al. ............ 600/407 |
| 2009/0252682 A1* | 10/2009 | Hillman ........................ 424/9.1 |

OTHER PUBLICATIONS

Duponchel et al., "Multivariate Curve Resolution Methods in Imaging Spectroscopy: Influence of Extraction Methods and Instrumental Perturbations," received May 16, 2003 for editing; published in J Chem. Inf. Comput. Sci., vol. 43, No. 6, pp. 2057-2067.

Fux et al., "Unmixing coral fluorescence emission spectra and predicting new spectra under different excitation conditions," received May 18, 1998 for editing; published in Applied Optics, vol. 38, No. 3, Jan. 20, 1999, pp. 486-494.

Gammon et al., "Spectral Unmixing of Multicolored Bioluminescence Emitted from Heterogeneous Biological Sources," received Nov. 10, 2005 for editing; published in Analytical Chemistry, vol. 78, No. 5, Mar. 1, 2006, pp. 1520-1527.

Jaumot et al., "A Graphical user-friendly interface for MCR-ALS: a new tool for multivariate curve resolution in MATLAB," received Oct. 22, 2004 for editing; published in Chemometrics and Intelligent Laboratory Systems, No. 76, pp. 101-110.

Jiang et al., "Self-modeling curve resolution (SMCR): Principles, techniques, and applications," Applied Spectroscopy Reviews, vol. 37, No. 3, 2002, pp. 321-345.

Keshava et al., "Spectral Unmixing," IEEE Signal Processing Magazine, Jan. 2002, pp. 44-57.

Kuo, "Three-dimensional reconstruction of in vivo bioluminescent sources based on multispectral imaging," received Aug. 7, 2006 for editing; published in Journal of Biomedical Optics, vol. 12(2) Mar./Apr. 2007, 12 pgs.

Lansford et al., "Resolution of multiple green fluorescent protein color variants and dyes using two-photon microscopy and imaging spectroscopy," received Feb. 15, 2001 for editing; published in Journal of Biomedical Optics, vol. 6, No. 3, Jul. 2001, pp. 311-318.

Mansfield et al., "Autofluorescence removal, multiplexing, and automated analysis methods for in-vivo fluorescence imaging," received Mar. 7, 2005 for editing; published in Journal of Biomedical Optics, 10(4), Jul./Aug. 2005, 9 pgs.

Nadrigny et al., "Detecting fluorescent protein expression and co-localisation on single secretory vesicles with linear spectral unmixing," received Aug. 18, 2005 for editing; published in Eur Biophys J, No. 35, Mar. 28, 2006, pp. 533-547.

Rice et al., "In Vivo imaging of light-emitting probes," received Jan. 26, 2001 for editing; published in Journal of Biomedical Optics 6(4), Oct. 2001, pp. 432-440.

Schrock et al., "Multicolor Spectral Karyotyping of Human Chromosomes," received Jan. 23, 1996 for editing; published in Science, vol. 273, Jul. 26, 1996, pp. 494-497.

Tauler et al., "Multivariate Curve Resolution Applied to Spectral Data from Multiple Runs of an Industrial Process," received Nov. 30, 1992 for editing; published in Analytical Chemistry, vol. 65, No. 15, Aug. 1, 1993, pp. 2040-2047.

Timlin et al., "Hyperspectral microarray scanning: impact on the accuracy and reliability of gene expression data," received Feb. 15, 2005 for editing; published in BMC Genomics 2005, 6:72, May 11, 2005, 11 pgs.

Troy et al., "Quantitative Comparison of the Sensitivity of Detection of Fluorescent and Bioluminescent Reporters in Animal Models," Molecular Imaging, vol. 3, No. 1, Jan. 2004, pp. 1-15.

Tsurui et al., "Seven-color Fluorescence Imaging of Tissue Samples Based on Fourier Spectroscopy and Singular Value Decomposition," received Jan. 14, 2000 for editing; published in The Journal of Histochemistry & Cytochemistry, vol. 48 (5), 2000, pp. 653-662.

Wentzell et al., "Multivariate curve resolution of time course microarray data," received Mar. 18, 2006 for editing; published in BMC Bioinformatics 2006, 7:343, Jul. 13, 2006, 19 pgs.

Zimmermann, "Spectral Imaging and Linear Unmixing in Light Microscopy," Adv Biochem Engin/Biotechnol (2005) 95:245-265.

International Search Report dated Jul. 24, 2008 from PCT Application No. PCT/US07/76813.

Written Opinion dated Jul. 24, 2008 from PCT Application No. PCT/US07/76813.

European Office Action for European Patent Application No. EP 08 745 172.0 dated Apr. 19, 2017.

* cited by examiner

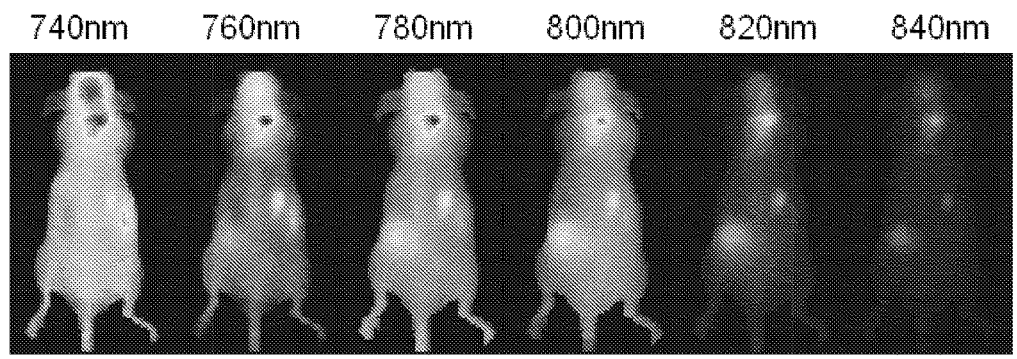
*Figure 9A*
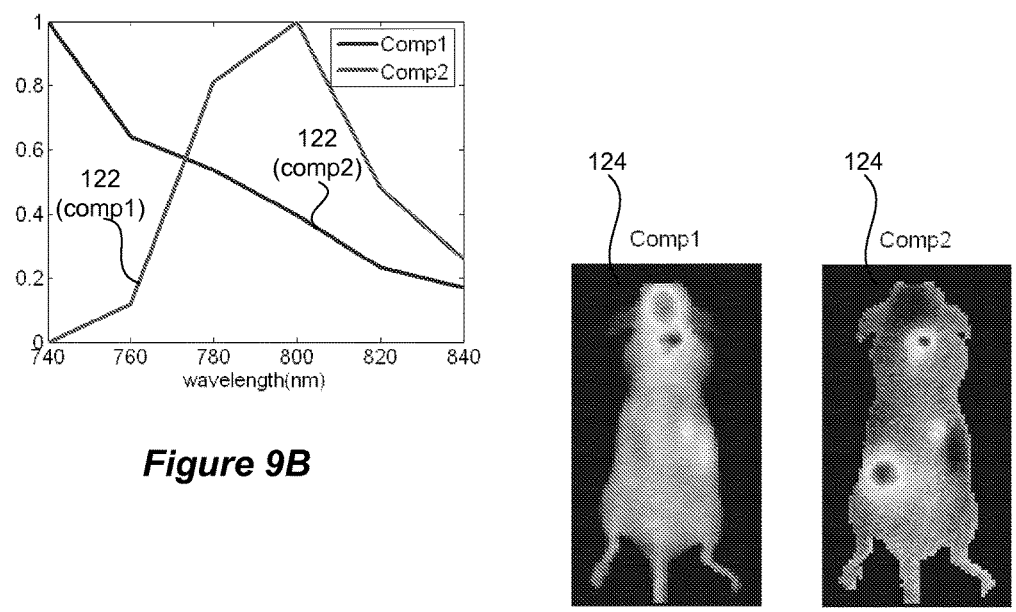
*Figure 9B*
*Figure 9C*

SPECTRAL UNMIXING FOR IN-VIVO IMAGING

CROSS-REFERENCE TO RELATED APPLICATIONS

This application claims priority under 35 U.S.C. 119(e) of U.S. Provisional Application No. 60/840,247 filed on Aug. 24, 2006 and titled "Fluorescent Imaging," which is incorporated by reference in its entirety for all purposes.

FIELD OF THE INVENTION

The present invention relates to spectral unmixing. In particular, embodiments described herein provide systems and methods that determine a spectrum for one or more light emitting reporters internal to an animal.

BACKGROUND

Imaging with light is gaining popularity in biomedical applications. One currently popular light imaging application involves the capture of low intensity light from a biological sample such as a mouse or other small animal. This technology is known as in vivo optical imaging. A light emitting probe inside the sample indicates where an activity of interest might be taking place. In one application, cancerous tumor cells are labeled with light emitting reporters or probes, such as bioluminescent luciferase or fluorescent proteins or dyes.

Photons emitted by labeled cells scatter in the tissue of the mammal, resulting in diffusive photon propagation through the tissue. As the photons diffuse, many are absorbed, but a fraction reaches the surface of the mammal, where they can be detected by a camera. Light imaging systems capture images that record the two-dimensional (2D) spatial distribution of the photons emitted from the surface.

Biophotonic imaging often captures image data produced by multiple internal light sources; each light source may have its own wavelength spectrum. When a camera captures an image from the multiple reporters, the resultant image mixes together light data from the various light sources. Even in the case of a single fluorescent probe in a mouse, tissue autofluorescence obscures light data ownership in an image. The indeterminate image data reduces the accuracy of subsequent processing that uses light data of a single source.

Overview

The present invention provides systems and methods for spectral unmixing of in vivo light data. The spectral unmixing separates image data according to spectra from multiple internal biophotonic light sources in an effort to isolate one or more spectra of interest. The spectral unmixing obtains multiple images, each captured with a different combination of excitation and emission wavelength bands. The spectral unmixing then uses an iterative solution process to separate spectra for the multiple internal light sources, and outputs a spectrum and/or a spatial distribution map for at least one of the internal light sources.

One use of the spectral unmixing pertains to fluorescent imaging to separate fluorescent image data before tomographic assessment.

In one aspect, embodiments herein describe a method for spectrally unmixing light data corresponding to light emitted from multiple light sources internal to an animal. The method selects an excitation wavelength band for excitation light provided to the animal, and selects an emission wavelength band that limits light spectra collected from the animal. The method then provides excitation light into the animal that is limited to the excitation wavelength band. The method captures a first image of at least a portion of the animal, where the first image includes light data that is limited in wavelength to the emission wavelength band and corresponds to light emitted by multiple fluorescent light sources internal to the animal. The method then changes the excitation and/or emission wavelength band. The method also captures at least one additional image of at least the portion of the animal that uses a different combination of excitation wavelength band and emission wavelength band for each additional image. Each additional image includes light data that corresponds to light emitted by the multiple fluorescent light sources internal to the animal and is limited in wavelength to the emission wavelength band of the different combination. The method uses an iterative solution process to unmix spectra for the multiple fluorescent light sources internal to the animal and to provide a spectrum for each light source.

In another aspect, embodiments herein describe a method for unmixing light data emitted from an animal. The method uses an iterative solution process to unmix spectra for the multiple fluorescent light sources internal to the animal to provide: a) a spectrum for a fluorescence probe light source internal to the animal, and b) a spatial distribution map for the fluorescence probe light source internal to the animal.

In another aspect, embodiments herein describe a method for spectrally unmixing light data corresponding to light emitted from multiple light sources internal to an animal. The multiple light sources may include a fluorescent or bioluminescent light source, for example. The method selects an emission wavelength band that limits light wavelengths collected from the animal. Then method also captures a first image of at least a portion of the animal, where the first image includes light data that is limited in wavelength to the emission wavelength band and corresponds to light emitted by the multiple light sources internal to the animal. The method changes the emission wavelength band. The method further includes capturing one or more additional images of at least the portion of the animal, using a different emission wavelength band for each additional image. Each additional image includes light data that corresponds to light emitted by the multiple light sources internal to the animal and is limited in wavelength to the different emission wavelength band. The method also uses an iterative solution process to unmix spectra for the multiple light sources internal to the animal to provide a spectrum for each light source. The iterative solution process implements a multivariate curve resolution and iteratively solves for a spectrum of each of the multiple light sources using finishing criteria.

In yet another aspect, embodiments herein describe logic encoded in one or more tangible media for execution and, when executed, operable to spectrally unmix light data corresponding to light emitted from multiple light sources internal to an animal.

In still another aspect, embodiments herein describe a method for obtaining a three dimensional representation of a light distribution located inside an animal that includes multiple light sources. The method spectrally unmixes light data emitted from the animal to produce spectrum data and a spatial distribution map for a fluorescent light source internal to the animal. The method obtains a three dimensional representation of a surface portion of the animal. The method maps fluorescent data from the spectrum data and spatial distribution map for the fluorescent light source to the three dimensional representation of the surface portion to create fluorescent light emission data from the surface portion of the animal. The method also determines a three-dimensional representation of a fluorescent probe distribution internal to the animal using the fluorescent light emission data and photon diffusion models.

In another aspect, embodiments herein describe an imaging system for obtaining a representation of a fluorescent probe distribution located inside an animal. The imaging system includes an imaging chamber and a processing system. The imaging chamber includes: a set of walls and a door that enclose an interior cavity, a stage configured to support the animal within the interior cavity, a camera, and a fluorescent excitation source. The processing system includes a processor and memory. The memory includes: instructions for selecting an excitation wavelength band for excitation light provided to the animal, instructions for selecting an emission wavelength band that limits light spectra collected from the animal, instructions for obtaining one or more fluorescent images using the camera, and instructions for unmixing spectra, using an iterative solution process, for the multiple fluorescent light sources internal to the animal to provide a spectrum for an internal fluorescent probe.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 9A-9C show sample animal data output from the method of FIG. 5.

DETAILED DESCRIPTION OF THE PREFERRED EMBODIMENTS

Figure 1:
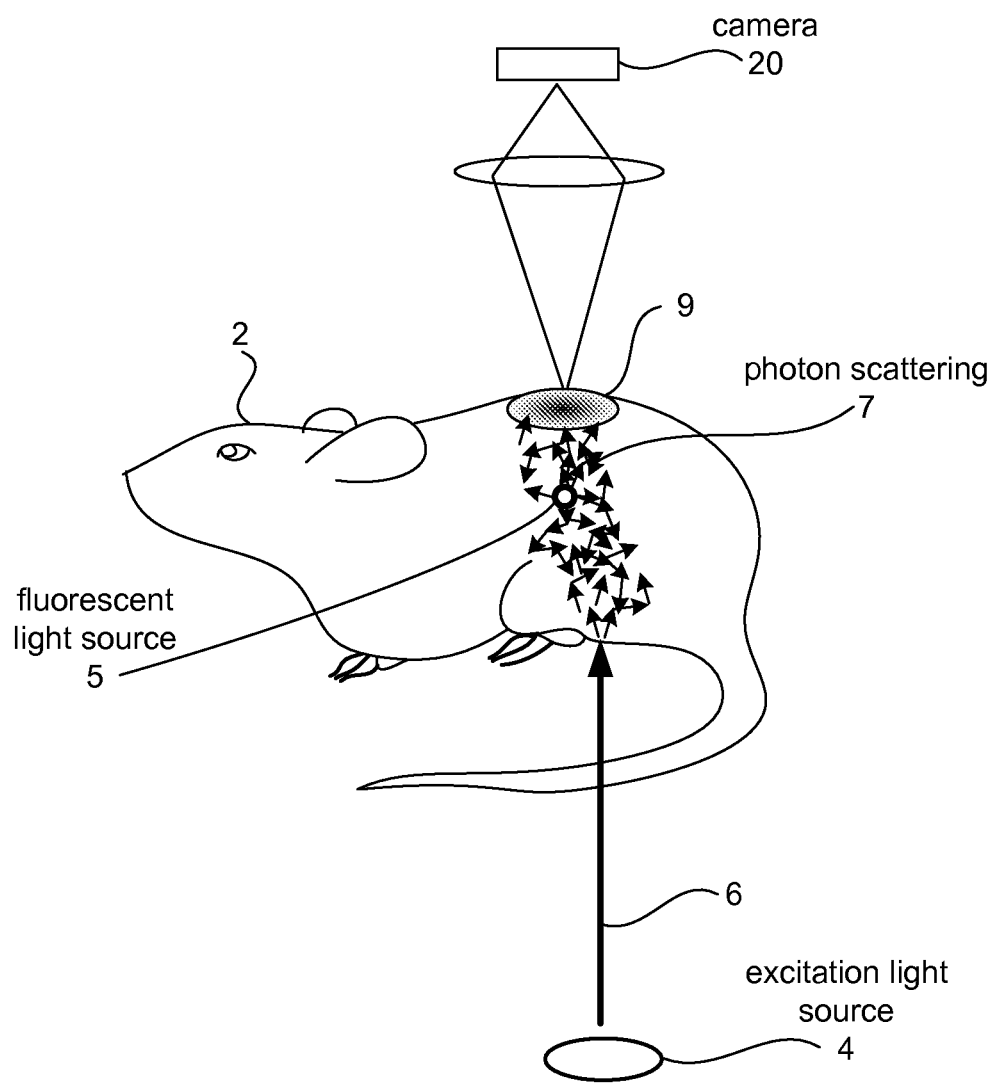
FIG. 1 shows a simplified pictorial of diffusive light propagation into, through, and out from, a mouse.

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Spectral unmixing embodiments described herein separate the contributions from multiple internal light sources and clean biophotonic image data from one or more in-vivo optical disturbances, such as autofluorescence. Spectral unmixing typically begins with the following question: is fluorophore A and/or fluorophore B and/or some other light source responsible for the light at pixel X? Spectral unmixing resolves the respective contributions for pixel X. While spectra for A's and B's might be known at an input level, the spectral unmixing tools compensate for light absorption within an animal, which affects the light data actually captured by a camera. More specifically, since the absorption of light in animal tissue depends on wavelength and depth, the output spectra of light from inside the mouse will vary with fluorescent probe depth. In other words, the spectra output from the mouse cannot be assumed solely based on the input light or fluorophore characteristics, which complicates spectral unmixing for in-vivo applications.

The spectral imaging techniques described herein overcome these challenges and are thus well suited to separate camera image data that includes both: a) light escaping from mouse due to autofluorescence of tissue in the mouse, and b) light escaping from the mouse due to one or more internal light sources of interest. The spectral imaging techniques may output pure component spectra and/or a 2D spatial distribution for each fluorophore or other internal light source.

The spectral unmixing processing may use a combination of excitation and emission filters to regulate the image data. This provides added solution data and confines inputs for spectral processing to known spectral limits. In another embodiment, spectral unmixing is expanded to include the acquisition of both reflectance and transillumination images with a variety of narrow-band excitation and emission filter options.

Typically, the fluorescent light from multiple sources is additive and separable by the spectral unmixing processing ($I = C_1 S_1 + C_2 S_2 + C_3 S_3 + \ldots$, where $C_n$ refers to the contribution of source spectrum, $S_n$). This is particularly relevant in in-vivo imaging since strong tissue absorption often non-linearly distorts the fluorescence emission wavelength band (relative to in vitro spectra, for example). In a specific embodiment, the spectral unmixing processing employs a linear model that is tolerant to non-linear tissue absorption. In another specific embodiment, the spectral unmixing uses multivariate curve resolution (MCR) and a least squares fitting algorithm to determine the respective contributions from fluorophore A and/or fluorophore B for pixel X.

The spectral unmixing maximizes sensitivity to fluorescent probes and other reporters. First, there is usually a limited amount of reporter that can be bound to tissue, and the spectral unmixing techniques described herein separate out these reporters for improved processing, which may permit the use of less reporter material. Second, it has the ability to separate spectral overlap of fluorescence signals; this is useful for overcoming tissue autofluorescence (broadband and strong) as well as detection of other reporters.

As the term is used herein, an internal light source refers to any object or substance in an animal that emits light. The emitted light may be the result of a light producing or biophotonic material, such as a light-emitting enzyme, a bioluminescent material, or a fluorescing material. One popular light-emitting enzyme is luciferase. In one embodiment, the light source includes a fluorescent light source (also referred to herein as a fluorescent entity) such as a fluorescent probe. The fluorescent probe may include a fluorescent marker such as a dye molecule, or a fluorescent reporter that produces fluorescent light based on gene expression. Tissue also acts as another internal fluorescent light source. Tissue autofluorescence refers to the natural fluorescence of substances within a material or organism. Mammalian tissue both absorbs and scatters light, and has autofluorescence properties that affect light propagation and in-vivo light imaging of both fluorescent and bioluminescent materials.

In one embodiment, a spectral unmixing tool is employed in software to separate spectral contributions from multiple sources. The spectral unmixing tool may be automated in software so as to reduce user labor. In this case, the software receives fluorescence image data from a camera or from memory, and processes the image data according to instructions stored in software and any input provided by a user for the unmixing. In a specific embodiment, a user initiates the spectral unmixing tool and software with an appropriate user interface command. After spectral unmixing, the multiple fluorophore contributions are separated and can be quantified using standard image processing tools, such as integrating the signal within a region of interest.

The spectral unmixing is also well suited for use in tomographic reconstruction. It permits fluorescent tomography (see FIG. 11) to process multiple light sources in a mouse independently, or to process the spectra of one light source free of the contributions of other light sources in the animal, such as autofluorescence or another light source. In another specific embodiment, spectral unmixing techniques described herein are automated, transparent to a user, and occur whenever a tomographic assessment is performed (and without spectral unmixing input from a user).

Systems and methods described herein unmix spectral data emitted from an animal. FIG. 1 shows a simplified pictorial of diffusive light propagation into, through, and out from, mouse 2.

Mouse 2 includes one or more internal fluorescent probes 5, which produce light that propagates in the mouse. A fluorescent probe distribution refers to light data that describes: an estimated light intensity of the fluorescent probe(s) 5 in mouse 2, an estimated location of the fluorescent probe(s) 5, an estimated size or shape of a distribution of fluorescent probe(s) 5, and/or spectral characteristics of the fluorescent probe(s) 5. Although the fluorescent light distribution in FIG. 1 shows a single probe 5, the mouse 2 may include multiple sites and fluorescent probes 5.

Fluorescent probe 5 generally refers to any object or molecule that produces fluorescent light. The fluorescent probe 5 absorbs incident energy of a certain wavelength or wavelength range and, in response, emits light energy at a different wavelength or wavelength range. The absorption of light is often referred to as the "excitation", while the emission light as the "emission". An output wavelength range is referred to herein as an 'output spectrum'. Fluorescent probe 5 may include one or more fluorescent light emitting molecules, called 'flourophores'. A flourophore refers to a molecule or a functional group in a molecule that absorbs energy of a specific wavelength and re-emits energy at a different wavelength. Many commercially available fluorophores are suitable for use with mouse 2. Suitable fluorophores include Qdot® 605, Qdot® 800, AlexaFluor® 680 and AlexaFluor® 750 as provided by Invitrogen of San Diego, Calif. Both organic and inorganic substances can exhibit fluorescent properties, and are suitable for use with fluorescent probe 5. In one embodiment, fluorescent probe 5 emits light in the range of about 400 nanometers to about 1300 nanometers.

The fluorescent probe distribution may be internal to any of a variety of light-emitting objects, animals or samples that contain light-emitting molecules. For example, the spectral unmixing techniques described herein are well-suited for use with in-vivo animals and in vitro well plates. Objects may include, for example, tissue culture plates and multi-well plates (including 96, 384 and 864 well plates). Animals including a fluorescent probe distribution may include mammals such as a human, a small mammal such as a mouse, cat, primate, dog, rat or other rodent. Other animals may include birds, zebra-fish, mosquitoes and fruit flies, for example. Other objects and samples are also suitable for use herein, such as eggs and plants. For ease of discussion, the remaining disclosure will show and describe a mouse 2 as an imaging object that contains a fluorescent probe.

In one embodiment, fluorescent probe 5 includes emits low-intensity light. In one embodiment, a low intensity fluorescent probe of the present invention emits light within mouse in the range of about $10^4$ to about $10^{14}$ photons/second, depending on probe concentration and excitation light intensity. For some imaging systems, a fluorescent probe 5 that emits flux in the range of about $10^4$ to about $10^{10}$ photons/second is suitable. Other light fluxes are permissible with the present invention. Photons/second is one unit of measure suitable to quantify the amount of light produced by probe 5; other units of measure are known to one of skill in the art, such as watts. In one embodiment, probe 5 emits light between about $10^{-15}$ to $10^{-6}$ watts of light. The amount of light produced by fluorescent probe 5 refers to the light emitted within mouse 2—not necessarily the amount of light generated by excitation light source 4 (such as an LED) that generates the light incident on the fluorescent probe 5.

Animal tissue is a turbid medium, meaning that photons are both absorbed and scattered as they propagate through tissue. An excitation light source 4 produces incident light 6 that enters a portion of mouse 2. The incident light 6 scatters in the mouse tissues and some of it eventually reaches an internal fluorescent probe 5. When excited by incident light 6, fluorescent probe 5 emits fluorescent light 7 from within mouse 2. The fluorescent photons 7 scatter and travel through tissue in the mouse to one or more surfaces 9; the light emitted from the surface may then be detected by a camera 20.

Thus, as light 6 and 7 diffuses through the mouse, some of the light is absorbed, but a fraction of the light propagates to a surface that faces the camera 20. For fluorescent imaging, there is a two-stage diffusion: a) incident light 6 from an incident surface to fluorescent probe 5, and b) emitted fluorescent light 7 from fluorescent probe 5 to the one or more surfaces 9.

A difficulty in tomographic imaging, and other in-vivo tasks, is that animal tissue autofluoresces. The autofluorescence may act as a source of background or noise to tomographic imaging of a fluorescent probe distribution, and techniques described herein separate the contributions of tissue autofluorescence from light emitted from the mouse surface. This isolates light emitted from the mouse surface corresponding to fluorescent probe 5, which provides a better input to tomographic reconstruction.

Figure 2:
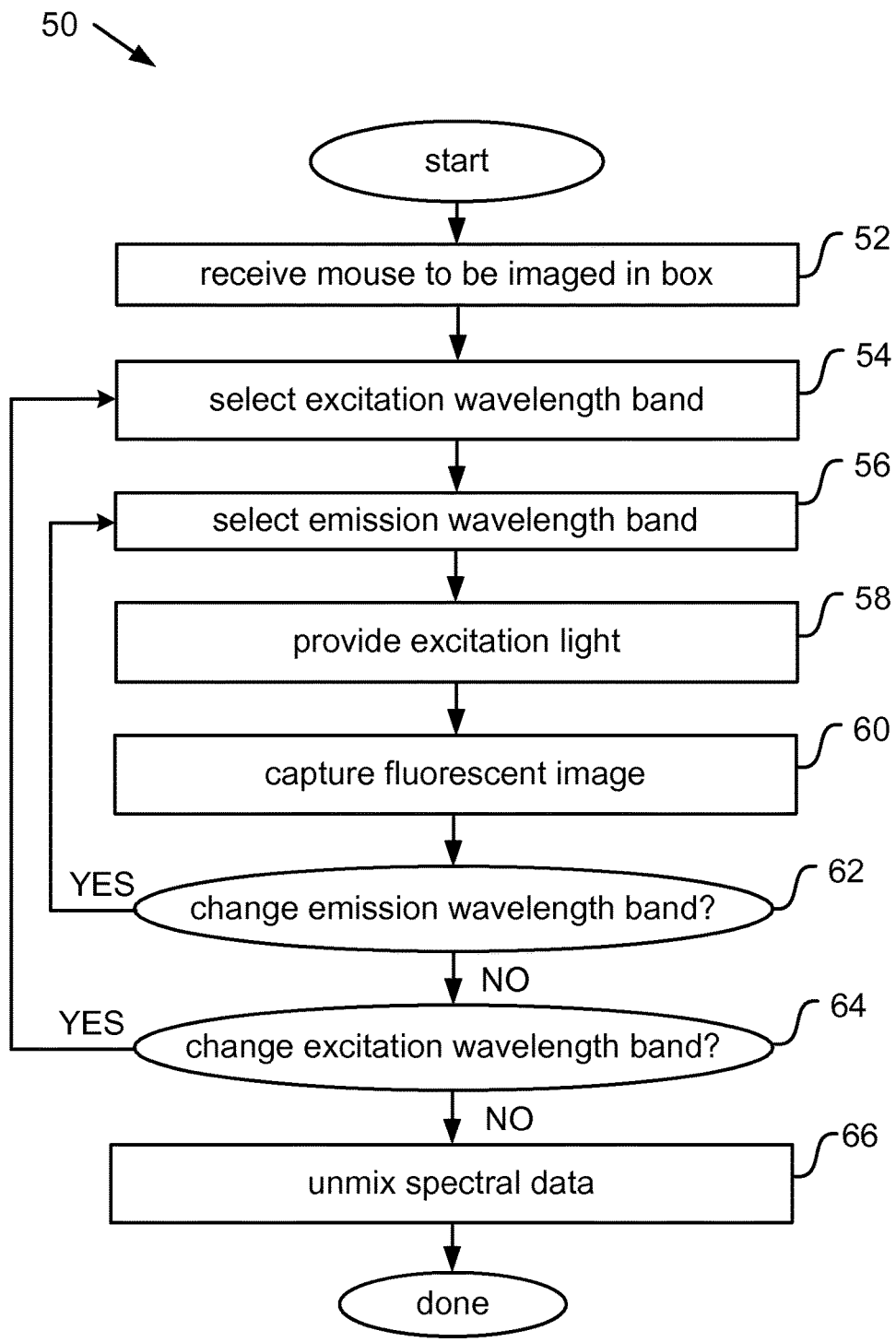
FIG. 2 shows a method for spectral unmixing according to one embodiment.

FIG. 2 shows a method 50 for spectral unmixing according to one embodiment. Spectral unmixing method 50 includes both image capture and image data processing to distinguish spectral contributions from separate light sources in a mouse.

Method 50 shows one particular method for image collection. In general, light and image collection may vary and spectral unmixing as described herein is not limited to any particular method of light and image collection.

Figure 12A:
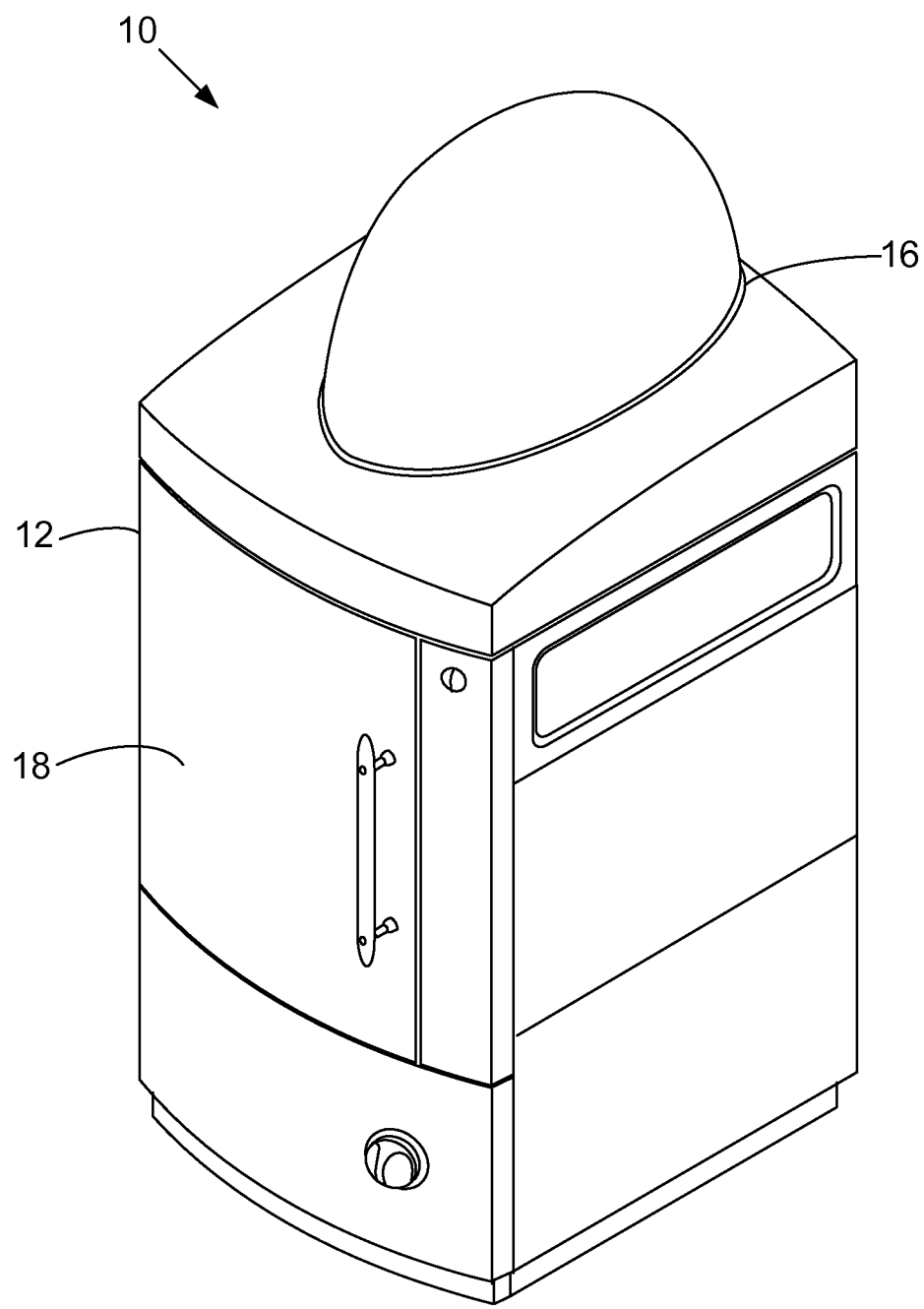
FIGS. 12A and 12B illustrate an imaging system configured to capture photographic, fluorescent and structured light images of a mouse in accordance with one embodiment of the present invention.

In a specific embodiment, image capture begins be receiving a mouse in an imaging box, such as that described below with respect to FIG. 12A (52). In one embodiment, image capture occurs with a mouse resting or lying on a horizontal stage or flat surface. The mouse may be anesthetized to prevent movement during imaging. For imaging box 10 of FIG. 12A, a user places the mouse on a stage within an imaging chamber for the imaging box. The user may also initiate image capture using a computer associated with the imaging system.

Spectral unmixing method 50 proceeds by selecting an excitation wavelength band for light provision into the mouse (54). The excitation wavelength band may be achieved using any combination of lights and/or filters. In one embodiment, an imaging system limits the excitation wavelength band by selecting an excitation filter for fluorescent image capture. The emission filter allows a user to control a spectrum of light provided into the mouse. In another embodiment, the light source responsible for producing excitation light includes a controlled spectra and no filter is needed. A filter wheel may be included in the imaging system to permit a user to change the excitation wavelength band limits. Changing excitation wavelength band is useful when two fluorophores have similar emission spectra but differ in their excitation spectra, such as quantum dots versus organic dyes. Other excitation wavelength band devices may be used other than filters. For example, liquid crystal filters or multiple excitation light sources (e.g., multiple LEDs) may be used.

Spectral unmixing method 50 also selects an emission wavelength band for fluorescent image capture (54). The selected emission wavelength band will depend on a number of factors such as the fluorophore used in the animal, tissue properties of the animal, whether an emission filter is used before the camera, etc. An emission filter, such as that shown in FIG. 3A, allows a user to control a spectrum of light received by the camera. An emission filter wheel may be included in the imaging system to permit a user to change the emission wavelength band limits. Other emission wavelength band devices may also be used.

Excitation light is then provided to the animal (58). Fluorescence imaging illuminates the mouse to excite fluorescence molecules in the internal fluorescent probe(s), and then captures an image of the mouse, or a portion thereof, as the internal probe fluoresces. Fluorescent image capture provides incident light onto into the mouse with an illumination source. The incident light should be large enough in magnitude to elicit a fluorescent from the probe, but not too large so as to saturate the camera. In response to the incident light, light emits from the "excited" fluorescent probe into the animal, and out of the animal for capture by a camera.

Figure 3A:
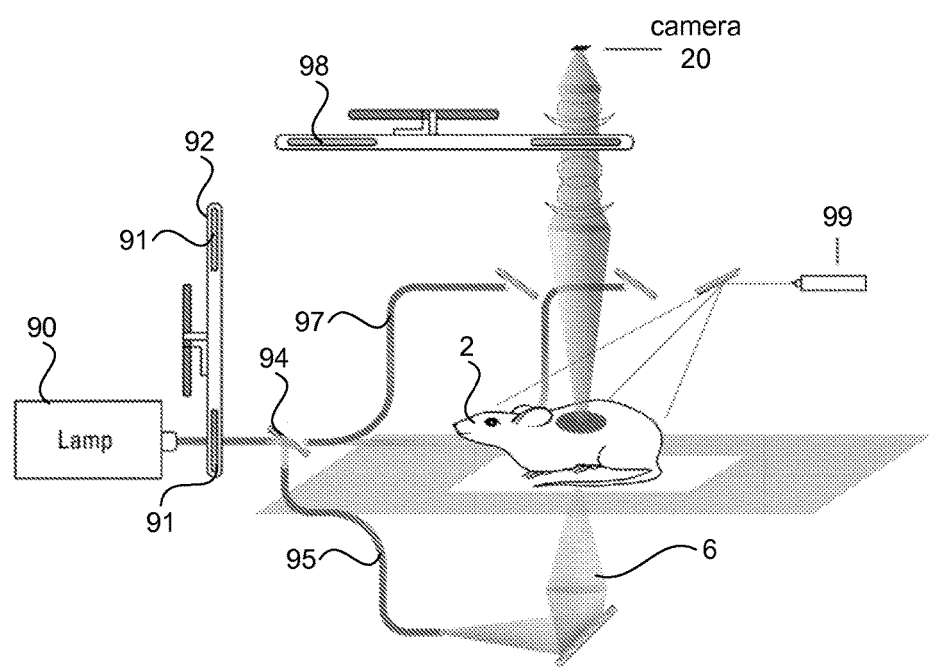
FIG. 3A schematically shows trans-illumination in accordance with a specific embodiment.

Spectral unmixing method 50 may use trans-illumination and/or epi-illumination. FIG. 3A schematically shows trans-illumination in accordance with a specific embodiment. Trans-illumination provides light from a side of the mouse opposite to the camera (e.g., incident light from below and a camera above), or into a portion of the mouse not visible to the camera, so that the excitation and emission light cumulatively travels through the mouse. This provides lower levels of autofluorescence. Also, the ability to move the transillumination point, relative to a fluorescent probe fixed within the animal, provides additional information that is use for 3D tomographic reconstructions. In this specific embodiment, the excitation light source 4 includes a lamp 90 that provides light that passes through a filter 91 in excitation filter wheel 92, which allows a user to change the wavelength band of incident excitation light by changing which filter intercepts the incoming excitation light. A fiber bundle switch 94 directs the excitation light into one of two paths 95 and 97. Path 95 is used for trans-illumination and directs the incident light along a fiber bundle or cable for provision towards a bottom surface of the mouse 2. In one embodiment, the outlet position of path 95 can be moved or re-directed to create multiple incident excitation light locations of trans-illumination path 95.

Figure 3B:
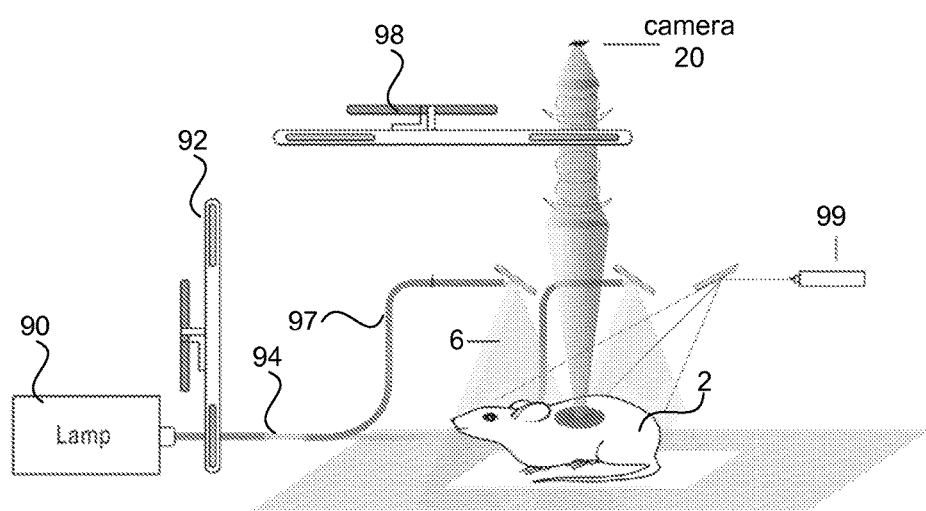
FIG. 3B schematically shows epi-illumination in accordance with another specific embodiment.

Epi-illumination provides incident light from the same side of the animal that an image is captured (e.g., incident light from above, and a camera above the mouse), or into a portion of the animal that is visible to the camera, and is often referred to as reflection-based fluorescent imaging. FIG. 3B schematically shows epi-illumination in accordance with another specific embodiment. In this case, switch 94 directs the excitation light into path 97, where it routes to a position above the mouse for provision towards a top surface of the mouse 2 on the same side of the mouse as camera 20.

Epi-illumination provides a faster survey of the entire animal, but may be subject to higher levels of autofluorescence. Epi-illumination also avoids significant light attenuation through the mouse. Software constraints based on this knowledge may then identify artifact voxels near the top surface, which are then removed by software. Additional detail on trans-illumination and epi-illumination fluorescent light sources suitable for use herein is further described in co-pending patent application Ser. No. 11/434,606 and entitled "A DUAL ILLUMINATION SYSTEM FOR AN IMAGING APPARATUS", which is incorporated by reference herein in its entirety for all purposes.

A camera then captures a fluorescent light image of at least a portion of the mouse (60). The fluorescent image records light output from the mouse as a function of 2D position. Light data in the image may include an original measurement in photon counts received by the camera, a calibrated measurement of radiance, or a fluorescent signal normalized to the incident photon intensity. Other measures and representations of the incident light on a camera may be used. The image may include the entire mouse, or a portion of interest that has been zoomed in on (optically or digitally). The image may be transferred to an image processing unit and/or computer for storage and subsequent processing.

Figure 5:
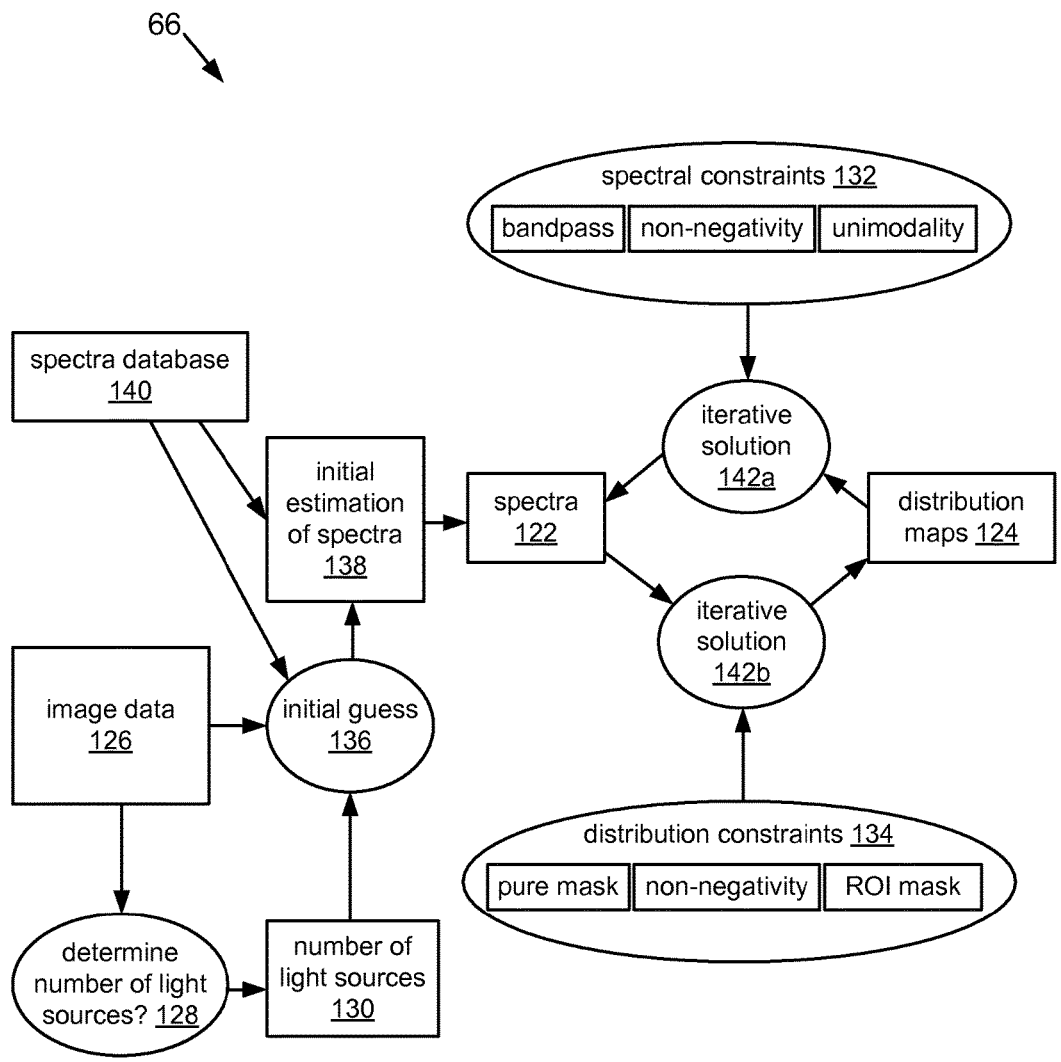
FIG. 5 shows a method for spectral unmixing in accordance with one embodiment.

Spectral unmixing method 50 may then continue by changing the combination of excitation wavelength band (62) and/or emission wavelength band (64) used in attaining an image. The combination of excitation filter wheel 92 and emission filter 98 allows images to be captured with different combinations of excitation and emission wavelength bands. Each filter combination provides a different set of input criteria and internal light conditions for spectral unmixing calculations (FIG. 5).

The number of different excitation and emission wavelength bands (e.g., filter combinations) and images may vary. In general, as more images are captured, more information is gathered for spectral unmixing. In one embodiment, a sequential scan of filters is launched to cover spectral features of all the fluorophores of interest. Sampled spectral peaks and valleys provide orthogonal spectral characteristics so that an unmixing algorithm can differentiate between different fluorophores. At the least, the number of different combinations is no less than the number of fluorophores. In a specific embodiment, successive and different combinations use a common excitation wavelength band and changing emission wavelength bands. In another specific embodiment, different combinations use a common emission wavelength band and changing excitation wavelength bands. Alternatively, multiple excitation wavelength bands and multiple emission wavelength bands may be used for the successive and different combinations.

The wavelength bands may be limited by hardware. In a specific embodiment, excitation filter wheel 92 includes twelve different filters while emission filter wheel 98 includes 24 different filters. In a specific embodiment, excitation filter wheel 92 includes ten 30 nanometer band-pass filters spaced every 35 nm from 430 to 745 nm and the emission filter wheel contains 20 nanometer band-pass filters ranging from 480 to 840 nm. Other hardware wavelength bands and arrangements are suitable for use. A processor associated with imaging system records which filters were used for image capture and associates a known bandwidth for each emission and excitation filter with an image.

In one embodiment, the fluorescent excitation uses a different wavelength band than the fluorescent emission. The bandgap between excitation and emission filters may vary with the imaging system used to capture the images. A bandgap of at least 25 nm is suitable for many systems.

Multiple fluorescent light images may thus be captured with the mouse in its current position (looping 62 to 56 to 60 and/or 64 to 54 to 60). All of the images may be used in spectral unmixing, or a subset can be used. The subset may be selected based on a quality measure for the images, such as a threshold for number of fluorescent photons collected in each image. Other quality measures may be used to select the images. The number of images captured may vary. In one embodiment, between two images and about twelve images are captured, where each image includes a different combination of excitation and/or emission spectra. In a specific embodiment, between two images and about five images are captured. The images may be stored for spectral unmixing at a later time, e.g., the images—or a subset thereof—are recalled from memory during spectral unmixing.

Method 50 then unmixes spectra for the multiple fluorescent light sources internal to the animal to provide a spectrum and/or 2D spatial distribution map for a light source of interest (66, and described further below with respect to FIG. 5).

Method 50 of FIG. 2 may include additional steps to improve spectral unmixing processing. In one embodiment, the transillumination location of the excitation light source is moved to capture multiple images of internal fluorescence and the same set of excitation and emission filters is used for the different excitation light source positions. This provides more input to the spectral unmixing processing.

Image capture may include additional steps for tomographic reconstruction, such as photographic and/or structured light image capture. A photographic image may be used in an overlay image that includes both the photographic image and fluorescent probe distribution. The overlay provides a simple pictorial view to facilitate user visualization of the internal fluorescent probe distribution. Structured light image capture is useful to build a surface topography for the mouse. In a specific embodiment, a structured light projection system projects structured light down onto the mouse from an angle, and the camera (also above the mouse, or on the same side of the mouse as the projector) captures the altered structured light. As shown in FIG. 3A, a structured light source 99 provides structured light onto the top of the animal for structured light image capture by the camera 20 without moving the mouse 2 on the horizontal surface. In addition, multiple images may be captured for differing trans-illumination positions of the excitation light source 4. Each trans-illumination position also provides a different set of input conditions to the tomographic reconstruction.

In another embodiment, the stage supporting the mouse is moveable, which allows camera 20 to capture images from multiple perspectives relative to the mouse 2. The stage may move in one dimension (e.g., up and down or side to side) or two dimensions for example. While the stage is at the second position, one or more photographic, structured light, and/or fluorescent images of the mouse may be captured. Excitation and emission filters may also be changed. For example, image capture may occur at anywhere from 2 to 200 positions of the mouse within an imaging chamber. Also, multiple structured light positions may be used to images more of the mouse in 3D. Eight positions, spaced every 45 degrees about a nose-to-tail axis of the mouse, is suitable in some 3D embodiments to build a stitched together surface representation for 360 degree viewing about the mouse.

In one embodiment, image capture and spectral unmixing is automated. A user may initiate software included with an imaging system that controls components of the imaging system responsible for image capture. For example, the user may launch imaging and acquisition software on a computer associated with the imaging system that initializes the camera and carries out imaging automatically. According to stored instructions, the software may then: select a desired stage position if a moveable stage is used; prepare the system for photographic, structured light, and/or fluorescent image capture (e.g., turn on/off lights in the box); focus a lens; selectively position an appropriate excitation and/or emission filter; select an excitation fluorescent light source (if multiple are present); set an f-stop; transfer and store the image data; perform spectral unmixing; build a reconstruction, etc. For fluorescent image capture, the camera may capture the fluorescent image quickly or over an extended period of time (up to several minutes).

Figure 4A:
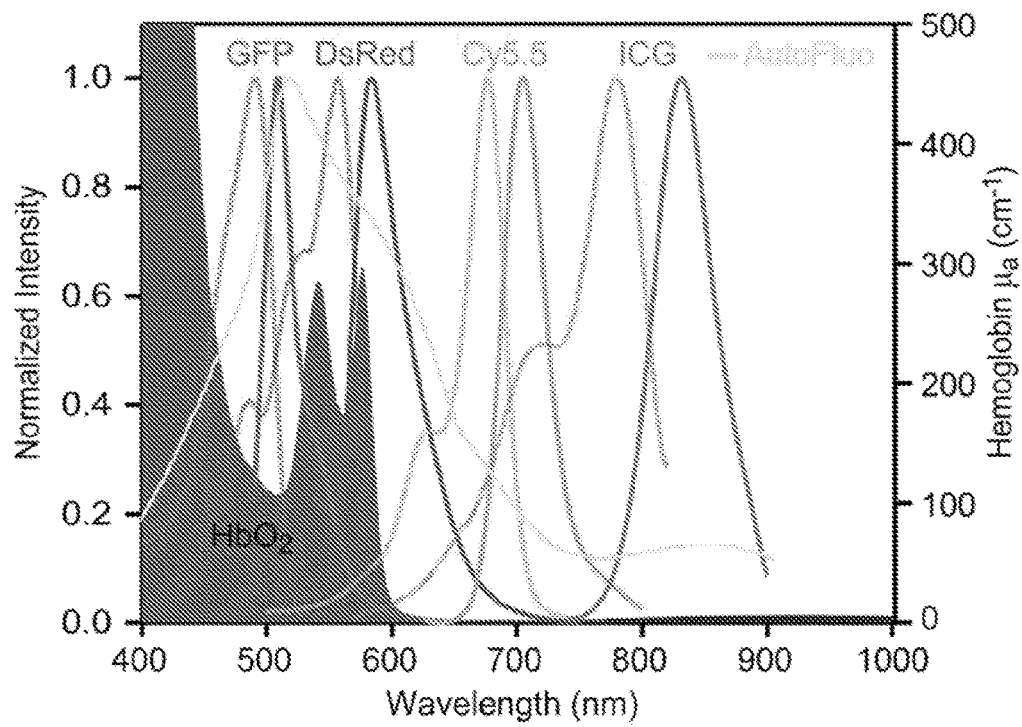
FIG. 4A shows a sample overlap of multiple types of fluorescence signals.
Figure 4B:
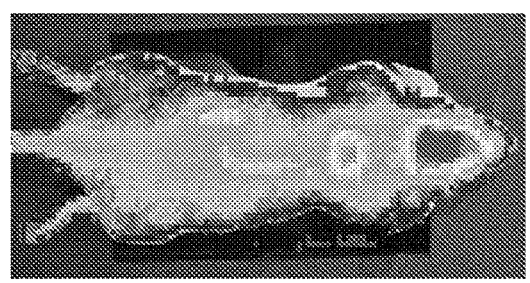
FIG. 4B shows a sample digital image that includes tissue autofluorescence in vivo.

FIG. 4A shows an example of the excitation and emission spectra for multiple types of fluorescence sources. A pictorial example of in vivo tissue autofluorescence is shown in the image of FIG. 4B.

Figure 6A:
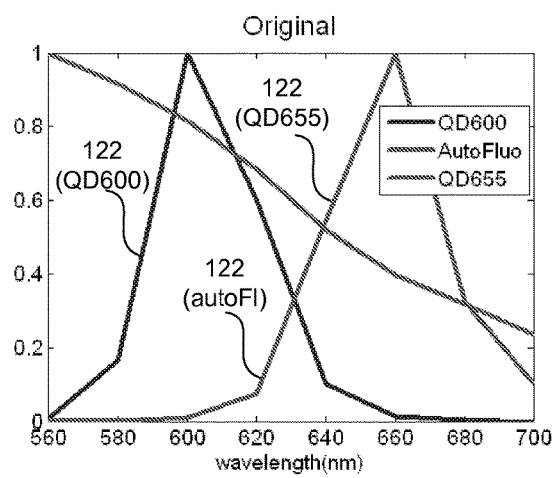
FIGS. 6A-6C show sample input data, images and output from the method of FIG. 5 to help illustrate the spectral unmixing.
Figure 6B:
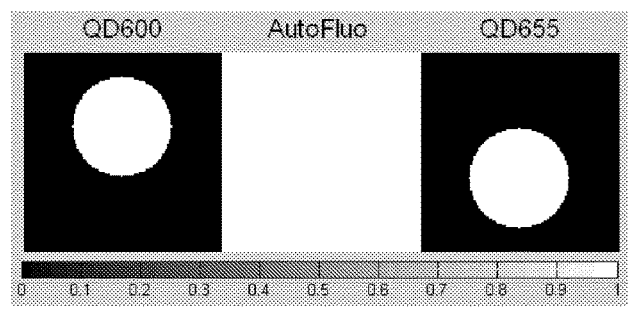
Figure 6C:
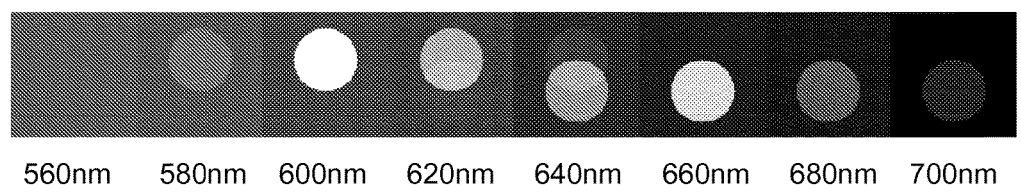

FIG. 5 shows a method 66 for spectral unmixing in accordance with one embodiment. FIGS. 6A-6C show sample input data, images and output from method 66 to help illustrate method 66. In the sample data of FIGS. 6A-6C, the data includes a mixture of three light sources: QDot600, QDot 655, and tissue autofluorescence. FIG. 6A shows the pure component spectra of each light source. FIG. 6B shows an actual spatial distribution map of each light source: QDot600 is distributed in an upper circle, QDot655 is distributed in a lower circle, and tissue autofluorescence is roughly uniform.

As mentioned above, the image collection excites a mixture including the light sources at one or more wavelengths, and for each wavelength, collects the emission in a select wavelength range. For the data of FIG. 6A, the spectral unmixing excites the mixture at a single wavelength and collects the emission at eight wavelengths from 560 nanometers to 700 nanometers, or every 20 nanometers. FIG. 6C shows eight spectral images, with poisson noise added.

Referring to FIG. 5, the output of spectral unmixing method 66 is a spectrum 122 for one or more light sources and a spatial distribution map 124 for the one or more light sources. As the term is used herein, a spectrum refers to a range of light for a light source, often characterized by an intensity for multiple wavelengths in the range. The spectrum may include intensity data for a light source over a wavelength range between about 400 nanometers and about 1300 nanometers. In a specific embodiment, each spectrum is normalized by its peak value and becomes unity at the peak wavelength, while a fraction is assigned to represent the measured signal of the light source at other wavelengths.

Spatial distribution map 124 refers to a two-dimensional data representation or other logical distribution of a light source in an image, which usually corresponds to photons emitted from the surface of the mouse. Isolated spatial distribution maps 124 provide better quantification and localization of light sources and greatly reduce the confusion generated by the autofluorescence in an image. When a peak wavelength is included in the multi-spectral analysis, distribution map 124 provides a consistent measure of the fluorophore signal regardless how many filters are used to unmix. Spatial distribution map 124 typically bears a limited relationship to the fluorophore spatial distribution map because the fluorescence yield varies with excitation and emission wavelengths and light transportation is affected by the surrounding tissue. While it is possible to correct the quantum yield with a simple calibration, however, this does not account for the light transportation, which is much more challenging and usually requires solving a complex 3D model. Thus, the distribution map should not be regarded as a measure of absolute fluorophore concentration but a tool to compare fluorescence sources at similar imaging conditions and comparable depths.

The input to method 66 shown in FIG. 5 includes an input data matrix, 126, as obtained from one or more fluorescent images. In a specific embodiment, the input data matrix includes fluorescent image data inserted into a matrix comprising the number of samples by the number of wavelengths. The samples refer to pixels in an image, resorted into one-dimension. The wavelengths refer to the excitation and emission wavelength pairs in a data sequence and usually relate to the number of spectral images in a dataset.

Spectral unmixing method 66 first determines (128) how many light sources 130, or components, exist in the data. Often, the data only includes two light sources 130: a fluorescent light source and tissue autofluorescence. However, multiple probes are present in many applications.

In a specific embodiment, spectral unmixing method 66 uses a principal component analysis (PCA) tool on the data matrix 126 to see how many light sources 130 exist in the data. PCA examines variance in the input data 126 as explained by a selected number of principal components. Since principal components are sorted in terms of the variance that they explain, when an additional principal component only affects a small margin of the total explained variance, the previous selected principal components have accounted for the real signals and the rest mainly contribute to random noise.

Figure 7A:
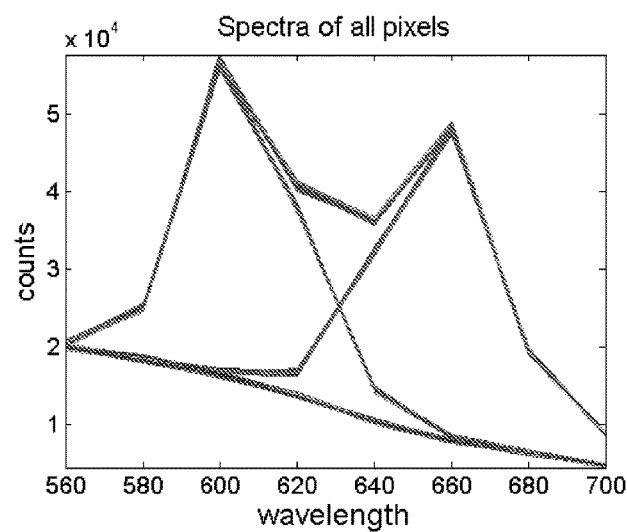
FIGS. 7A-7C illustrate sample output from a principle component analysis in accordance with a specific embodiment.
Figure 7B:
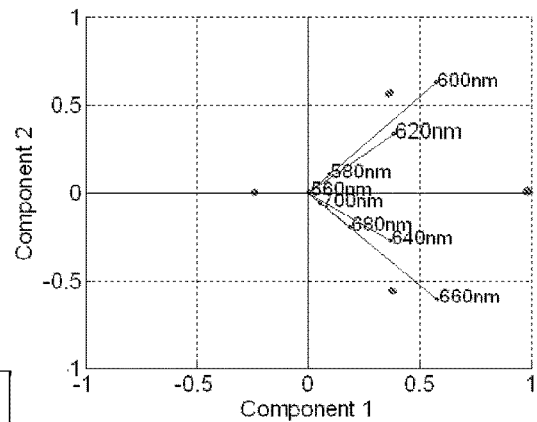
Figure 7C:
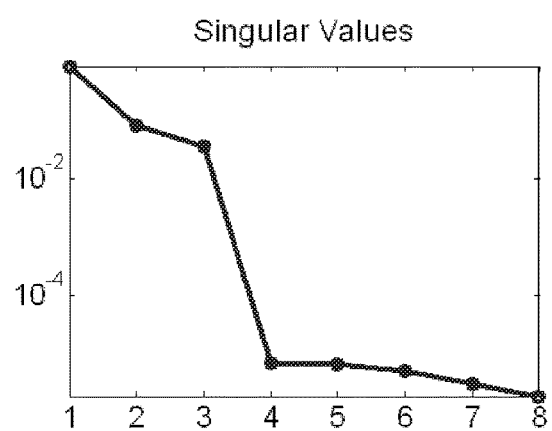

FIGS. 7A-7C illustrate sample output from the principle component analysis. FIG. 7A plots all the spectra for all the pixels. FIG. 7B shows a bi-plot that visualizes both the principal component coefficients for each variable and the principal component scores for each observation in a single plot. FIG. 7C shows a singular values plot vs. number of light sources. In this instance, there is sharp drop at 4, indicating only three major light sources in the data 126 for FIGS. 7A-7C.

Principal components are orthogonal to each other, although they do not have biological meanings, they imply the independent real components present in the data. The PCA may also illuminate which wavelengths are important and useful to separate the light sources from other interference signals. For method 66, PCA analysis is implemented as a complimentary tool, but not relied on.

Other approaches can be used to determine (128) the number of underlying light sources (130). Since most in vivo imaging experiments are often designed and users have the knowledge of the fluorophores used, another technique to determine the number of sources 130 lets a user input the number. In addition, if the PCA result is not satisfactory, a user can manually adjust the number and repeat the analysis.

After estimating the number of light sources 130, method 66 determines the size of the problem domain. This is done by multiplying a distribution profile, C, and pure spectra matrix, S. In this case, the distribution profile, C, is a matrix comprising the number of samples (or pixels) by the number of light sources 130, and each column represents the contribution of the corresponding light source, which can be re-interpreted into a 2D distribution map. The pure spectra matrix, S, is a matrix comprising the number of samples light sources 130 by the number of wavelengths, and each row represents the pure component spectrum of this light source. As mentioned above, the distribution profile 124 and spectra matrix 122 will also be the output of spectral unmixing method 66.

Method 66 then provides an initial estimation 136 for spectra. Beforehand, the spectral unmixing may classify the data, which helps with an initial guess for iterative processing. Suitable techniques used to classify the data may include Kmean clustering or distance between samples, for example. Other techniques may be used.

When iterative solution process 142 uses MCR and ALS, the iteration is sensitive to the selection of an initial estimate $S_0$ for the spectra in initial guess 136; different initial estimates may lead to different solutions, mainly because there are often multiple local minimums in a solution space for such a high degree of freedom problem. There are several approaches to find a suitable initial estimate 136. The initial estimation 136 may use: the input data 126 and a clustering method, a random sampling, and/or an a priori spectra database 140 that includes historical initial estimates that have worked well. Another systematic initial estimate uses an evolving factor analysis (EFA) and SIMPLISMA to extract the pure component spectra. To make the initial estimate close to the true solution and stable, another approach uses a statistical data analysis and k-means clustering method. This partitions the dataset 126 into k groups on a measure of distance between samples; the centroids of these groups are used as the initial estimate. The distance measure determines how the similarity of two samples is calculated. A correlation distance measure may be chosen because it emphasizes the spectrum shape and is not affected by the scaling due to the contribution. Alternatively, an initial estimate $S_0$ for the spectra can be loaded from an a priori spectra library, or from a spectra in a user selected region of interest (ROI) of the image. This latter option gives the user more control to the unmixing algorithm, which is useful for in vitro imaging where pure components are relatively easy to determine and pure spectra do not change significantly. The initial estimate may also be fixed when: all the spectra are fixed, the iterative alternating least squares (ALS) degenerates to single step least squares, and thus method 66 is simplified to a popular linear unmixing algorithm in fluorescence microscopy. The initial estimation 136 produces an initial spectra estimate $S_0$ 138.

Method 66 then uses an iterative process (142) that solves the problem C*S=D where C and S are both unknown. It is an under-determined system and infinite solutions exist. One suitable output is then a best approximate solution of the linear system given one or more constraints. In one embodiment, an iterative solver is used. The iterative solver may use any conventional finishing criteria, such as a least squares error approximation.

In one embodiment, method 66 uses multivariate curve resolution (MCR) and alternating least squares techniques (ALS) to produce the output spectra 122 and spatial distribution map 124 for a contributing light source. In a specific embodiment, iterative solution process 142 solves for two alternating least-square problems: loop 142a) minimizing of C*S=D over S for given C; and loop 142b) minimization of C*S=D over C for given S. This technique neither relies on pre-measured in vitro spectra of light sources nor requires manually selection of pure components. Similar to principal component analysis (PCA), MCR explains the data variance with some principal components, but, differently, it finds realistic components instead of mathematical ones. With input of multi-spectral images 126 and a few constraints 132 and 134, the unmixing method 66 automatically outputs the pure spectra 122 and a spatial distribution map 124 of each internal light source.

To help converge to a unique and realistic solution, method 66 adds one or more constraints 132 and 134 to the iteration process. Constraints 132 and 134 may come from knowledge about the variables, such as non-negativity. The constraints reduce the solution space by enforcing some boundaries and help solve the rotation ambiguity inherent in a bilinear model. Here, the rotation ambiguity refers to the fact that any arbitrary k by k orthogonal matrix Q ($Q^TQ=I$, I is identity matrix) can result another suitable solution $CQ^T$ and QS for the bilinear model. A special case of the rotation ambiguity that Q is a diagonal matrix is often known as the scaling ambiguity. Usually this cannot be solved by setting the constraints and thus a normalization procedure may be enforced on either C or S throughout the iteration. The convergence is achieved when the absolute change of a residual norm $e^2$ or some other error assessment passes below a threshold (e.g., 0.1% error). After convergence, method 66 outputs matrices for C and S, which represent the output spectra 122 and spatial distribution maps 124, respectively.

Thus, as an underdetermined system, output improves as spectral unmixing method 66 knows more about the data. In general, the constraints 132 and 134 may include any limit on the modeling and solution-space. In one embodiment, the constraint limits internal light modeling by one or more practical considerations.

In one embodiment, the constraint includes a spectral limit 132. One suitable spectral constraint is non-negativity that limits both spectra and distributions to non-negative numbers. Non-negativity constraints are applied after each calculation for S or C using least squares method $S=(C^TC)^{-1}_1C^TD$ or $C^T=(SS^T)^{-1}SD^T$. Instead of setting negative elements to zero, a more rigorous method non-negative least squares (NNLS) is used to recalculate the solution at the columns of S or the rows of C where comprise negative elements rather than the whole matrix.

A unimodality spectral constraint 132 limits the spectrum for each light source to a single peak, which has a monotonic and smoothing effect. Unimodality constraints are suitable for fluorescence spectra since fluorophores usually only have single excitation or emission peak. Typically, a user has a priori knowledge about the fluorescent light sources, such as input spectra for the fluorescent reporters stored in a database 140. For automated spectral unmixing, fluorophore(s) used in the fluorescent probe are typically known for an imaging application, and optical properties for the fluorophore wavelengths are also known and stored in software. Other known fluorophore properties may include excitation wavelength band and extinction coefficient and quantum efficiency, for example.

Another spectral constraint 132 uses a bandpass constraint, which limits the spectral data input to the iterative solution process to within a desired wavelength range. In a specific embodiment, the bandpass constraint relates to a known fluorophore used in the animal. The emission wavelength band of most fluorophores has a sharp increase from a shorter wavelength range to its emission peak, after which it decreases relatively slowly towards longer wavelengths. If the fluorophore is known, a high pass filter may be used to suppress the unwanted spectrum below its rising edge. Similarly, for most fluorescent dyes, low pass filter can be used when solving for excitation wavelength band to eliminate higher wavelength values.

Bandpass constraint information may also come from the filter combination used in image capture. A predetermined wavelength range for a wavelength filter used in image capture (and the spectrum properties for the fluorophore at that wavelength range) may then be input to iterative solution 142.

In a specific embodiment, the imaging process is automated and a computer recalls spectrum constraints 132 for the filter and fluorophore from memory. A graphical user interface associated with the imaging system allows a user to select one or more fluorophores or filters from a list, where information for each fluorophore and filter is stored in a database.

In another embodiment, the constraint is applied to the spatial light distribution map 134. For example, an image or equality constraint may also be applied, which limits the light values within explicit spatial boundaries of the spatial distribution map. This may include: a spatial image limit (e.g., the region of pure component samples that can be selected), a region of interest analysis that defines a 2D spatial image limit in the image, a pass band for an individual spectrum, etc. A pure mask constraint 134, assigned to a light source, determines an image region that only contains a particular light source. In other words, the contribution of other light sources in this mask is zero. An ROI mask associated with a component determines a region in the image that this component might exist, in other words, outside of this mask the contribution of a component is zero.

Method 66 also applies the selected spatial distribution map constraints 134 to the intended light source 130. For example, assuming there are two components, one is the tissue autofluorescence with a broad spectrum and the other is a red fluorescent dye with a sharp spectrum, method 66 ensures that an ROI constraint is applied to the dye not autofluorescence. This stems a component-wise rotation ambiguity and crisis regarding mismatch between the initial estimate and its constraints. To disentangle such ambiguity, spectra are automatically sorted in each iteration 142 in ascending order of their center wavelengths (power weighted average), i.e., by the color of the fluorophores. In this example, the red fluorescent dye is tagged next to a yellowish autofluorescence and the user or software can easily apply constraints.

Figure 8A:
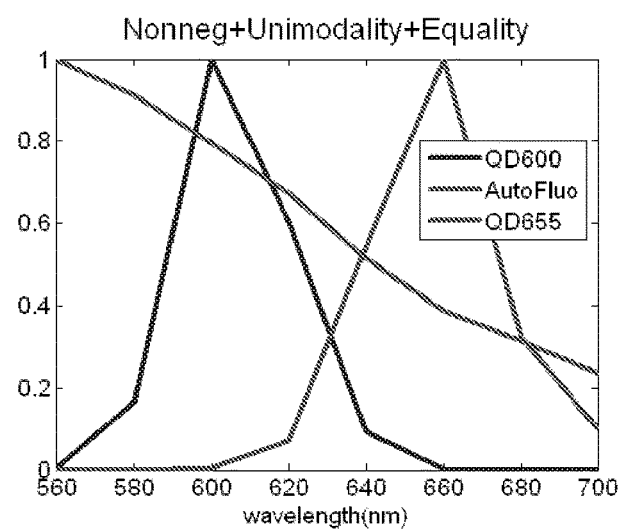
FIGS. 8A and 8B show the unmixed spectral results when non-negativity, unimodality and equality constraints are applied in accordance with a specific embodiment.
Figure 8B:
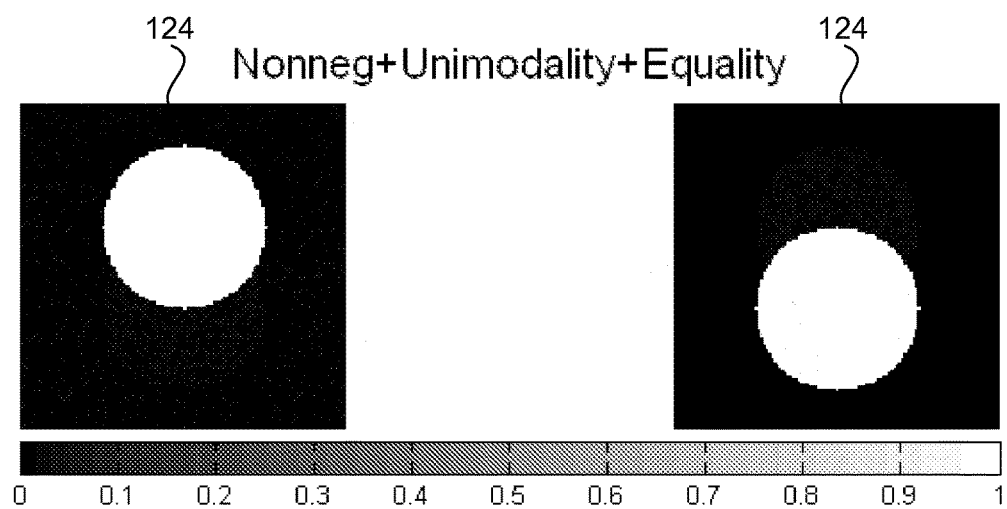

FIGS. 8A and 8B show the unmixed spectral results (spectrum 122 and spatial distribution map 124) when non-negativity, unimodality and equality constraints are applied. Because the spectral unmixing knows QD655 has no emission below 600 nm, and QD600 has no emission above 660 nm, the spectral unmixing adds a passband constraint to each spectrum. It is an equality constraint to convert data to zero—for each spectrum outside of the pass band. With these new constraints, the unmixed results improve significantly and closely resemble the original spectra shown in FIGS. 6A and 6B.

FIGS. 9A-9C show sample mouse data and mouse output for method 66. FIG. 9A shows six sample emission input images, ranging from 740 nanometers to 840 nanometers (excitation was at 675 nanometers) and captured in reflection mode. Unmixing the images with only non-negativity constraints produces two light spectra 122, as shown in FIG. 9B, where Comp1 represents an autofluorescence signal, and Comp2 represents the signal from a fluorescent dye (Alexa fluor 750). FIG. 9C shows sample spatial distribution maps 124 output generated using the output of spectral unmixing method 66.

As mentioned above, spectral unmixing method 50 captures multiple images with different excitation spectra (62 in FIG. 5) and/or emission spectra (64). Filtration of the incoming excitation and/or emission light also allows color rendering of the fluorescent spectra produced from a mouse using only a monochrome camera. In other words, placing a filter (with a known narrowband spectrum) in front of the emitted light permits color data collection according to the filter currently being imaged through. This may improve user perception of the data.

Figure 10A:
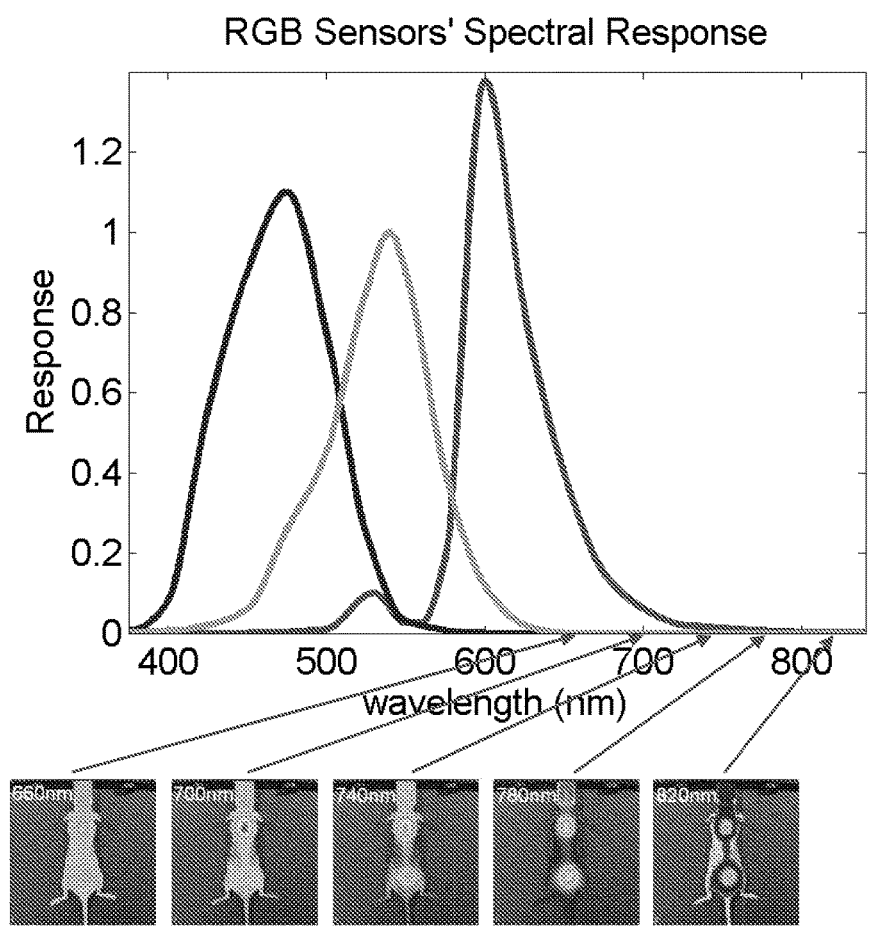
FIG. 10A shows five images that each correspond to an image produced by filtration about a frequency shown in each image.
Figure 10B:
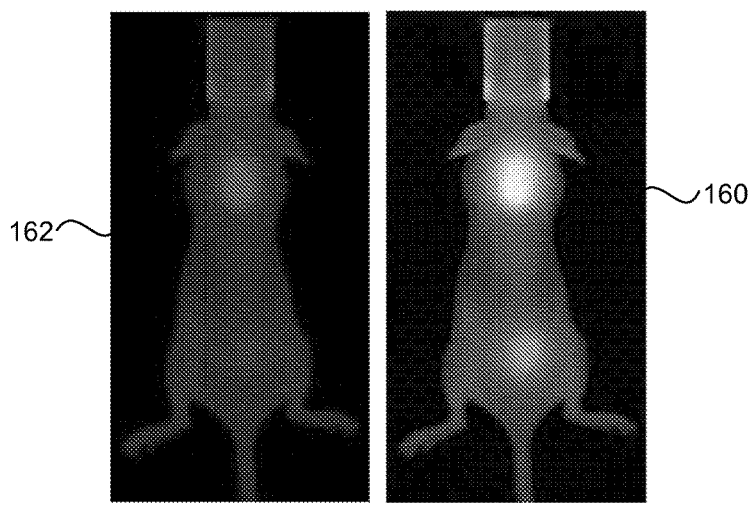
FIG. 10B shows a real color image produced by a color camera without light filtration and an image produced by the images of FIG. 10A.

FIG. 10A shows five images that each correspond to an image produced by filtration about a frequency shown in each image. Separation of the incoming colored light produces one colored image according to each filter. The data from each filtered image may then be recombined to assemble an adaptive color image 160 as shown in FIG. 10B. FIG. 10B also shows a real color image 162 produced by color camera. The adaptive color image 162 uses a different color map assembled from the image data gained via multiple filters, and more visibly shows the two separate probes in a mouse. The reconstructed image 160 may then be pictorially displayed to a person, where the person's eye may then spectrally unmix the image 160 and discern the two separate probes.

Figure 11:
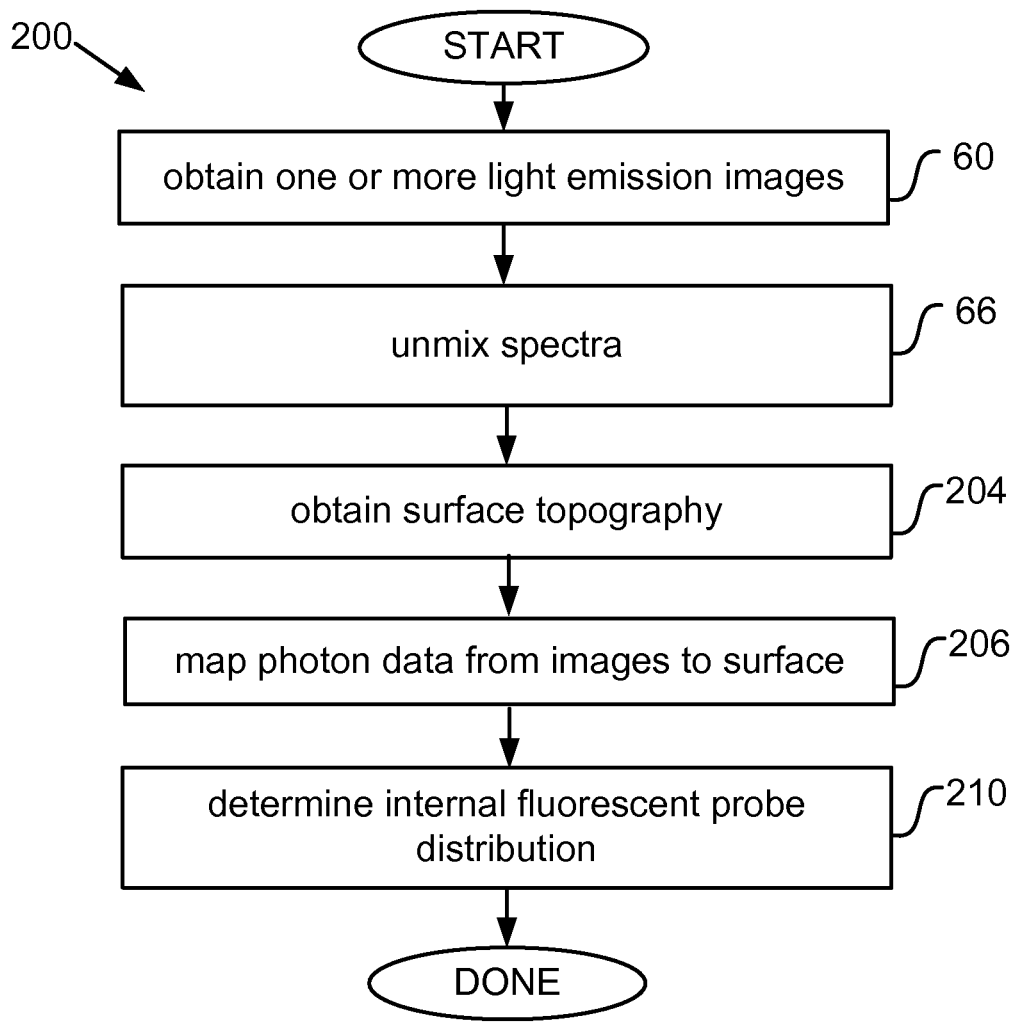
FIG. 11 illustrates a method for obtaining a three dimensional representation of a fluorescent light distribution located inside a mouse in accordance with a specific embodiment.

Spectral unmixing as described herein is well suited to output data that serves as an input for tomographic reconstruction of an internal light source. FIG. 11 illustrates a method 200 for obtaining a 3D representation of a fluorescent light distribution located inside a mouse in accordance with a specific embodiment.

Method 200 obtains one or more fluorescent images of at least a portion of the mouse (60). The images include fluorescent image data that describes fluorescent light emitted from the mouse. The images may be recalled from memory (previously captured) and/or captured in real time by a camera and imaging system, such as that described below with respect to FIGS. 12A and 12B. FIG. 2 describes image capture in further detail.

Spectral unmixing occurs as described above with respect to FIG. 5 (66).

Method 200 maps the separated 2D fluorescent image data from step 66 onto a surface of the mouse (206). Before the mapping can occur, method 200 obtains a surface representation of at least a portion of the mouse (204). The surface portion may include all of the mouse, or a smaller portion. Typically, this portion includes parts of the mouse that the fluorescent image data will be mapped onto.

In this case, the methods also employ topographic determination tools. Topographic imaging determines a surface representation of an object, or a portion thereof. In one embodiment, the present invention uses structured light to determine a surface topography for at least a portion of the mouse. Tomographic imaging refers to information inside the mouse surface. An exemplary illustration of topographic vs. tomographic imaging uses a 2D planar slice through the mouse: topography gives the surface (the outer bounding line), while tomography provides information inside the bounding surface.

The surface representation refers to a mathematical description or approximation of the actual surface of the mouse, or a portion thereof. The surface representation need not include the entire mouse, and may include a portion of the mouse relevant to a particular imaging scenario. Suitable techniques to obtain a surface representation include structured light, or another imaging modality such as computer tomography (CT) or magnetic resonance imaging (MRI), for example. The surface representation may be divided into a surface mesh comprising a set of surface elements, as will be described below.

In one embodiment, structured light is used to obtain a surface representation of the mouse. Structured light uses a set of lines of light that are projected down on the mouse at an angle (at about 30 degrees, for example) to the surface normal. The mouse generates structured light surface information as each light line reacts to the shape of the animal. Cumulatively, the lines of light each bend or alter in spacing as they pass over the mouse. The structured light surface information can be measured by a camera and used to determine the height of the surface at surface portions of the mouse that are illuminated by the structured light source. These surface portions are the portions of the mouse that face the camera (for a current position of the mouse relative to the camera). The position of the mouse relative to the camera may be changed to gain multiple structured light images and structured light information from multiple views.

A camera captures the structured light surface information, digitizes the information and produces one or more structured light images. A processor, operating from stored instructions, produces a 3D surface representation of the mouse—or a portion of the object facing the camera—using the structured light information. More specifically, a processing system, running on stored instructions for generating a topographic representation (a surface map) from the structured light surface information, builds a 3D topographic representation of the mouse using the structured light surface information. If multiple views are used, structured light topographies from these multiple views may be "stitched together" to provide a fuller surface representation from different angles. Structured light image capture, hardware and processing suitable for use with a mouse is described further in commonly owned and pending patent application Ser. No. 11/127,842 and entitled "Structured Light Imaging Apparatus", which is incorporated herein by reference in its entirety.

Once the surface topography is determined, process flow 200 maps the separated fluorescent image data in the 2D fluorescent images to fluorescent image data at a surface of the mouse (206). This converts 2D light data collected at a camera to 3D light data at a 3D surface of the mouse. In one embodiment, the mapping converts radiance data from the fluorescent images to photon density just inside the surface. The mapping manipulates 2D camera data according to the geometry between the mouse surface and the camera lens to derive values of the light emission intensity (or radiance) at the surface.

Emission of light from a mouse surface may be specified in units of radiance, such as photons/sec/cm$^2$/steradian. In one embodiment, an imaging system captures images of the mouse and reports surface intensity in units of radiance. Surface radiance can be converted to photon density just inside the mouse surface, using a model for photon propagation at the tissue-air interface, as described below. When the surface representation includes a set of surface elements, the mapping may produce a surface emission data vector that includes photon density at each surface element for the mouse topography. The photon density just inside the surface are then related to a light emitting probe distribution inside the mouse tissue using a diffusion model.

After the spectra for each fluorescent probe 5 has been separated, and autofluorescence has been determined and separated from the fluorescent probe spectra, the separated fluorescent probe emission contributions as mapped to the surface can be used for tomographic processing. In a specific embodiment, method 200 subtracts tissue autofluorescence from the light emitted from the surface (as calculated in 206), which isolates the light/signal due to each fluorescent probe 5.

Method 200 then calculates a 3D representation of the fluorescent probe distribution internal to the mouse (210). As the term is used herein, a fluorescent probe distribution refers to a description or mathematical depiction of fluorescent light emitters inside the mouse. Typically, the fluorescent light corresponds to a fluorescent probe disposed inside the animal. The fluorescent probe may include a fluorescent marker such as a dye molecule, or a fluorescent reporter that produces fluorescent light based on gene expression.

Light data internal to the mouse 2 surface generally refers to mathematical representation or approximation of light within the mouse 2 interior. This may include a set of points or volume elements, each characterized by 3D position and source strength. In one embodiment, the present invention divides the mouse 2 interior into volume elements where each volume element is considered to contain a point light source at its center. A solid mesh of these volume elements then defines a collection of point sources used to approximate light data internal to the mouse and the actual probe distribution within mouse 2. For example, a solid mesh of cubic volume elements may be used.

Method 200 uses the fluorescent light emission data from the mouse surface, along with tomographic imaging software that models light propagation internal to the mouse and solves for fluorescent probe distribution. The internal light propagation modeling includes both a) fluorescent excitation light propagation from the excitation light source 4, and its entry points into the mouse, to the fluorescent probe 5, and b) fluorescent emission light propagation from the fluorescent probe 5 to the surfaces captured in the fluorescent images.

Tomographic modeling, processing, and fluorescent probe determination of step 210 is described in further detail below with respect to co-pending patent application Ser. No. 11/733,358 entitled "FLUORESCENT LIGHT TOMOGRAPHY", which is incorporated by reference in its entirety for all purposes.

Figure 12B:
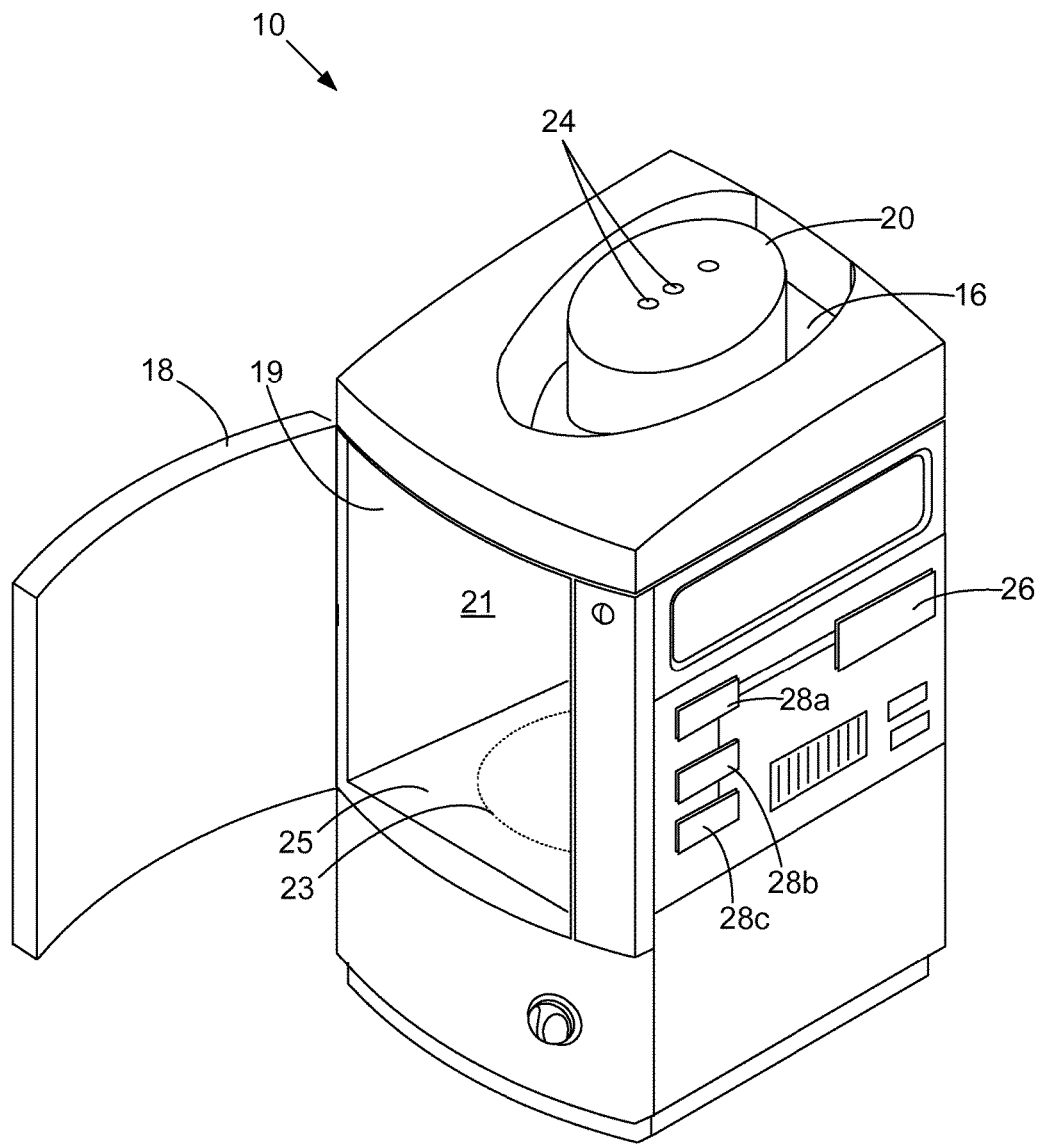

The spectral unmixing techniques of the present invention are typically implemented by a suitable processor or computer-based apparatus. FIGS. 12A and 12B illustrate an imaging system 10 configured to capture photographic, fluorescent and structured light images of a mouse in accordance with one embodiment of the present invention. While spectral unmixing will now be described with respect to imaging system 10, it is understood that the spectral unmixing as described herein is well suited for use with other imaging systems.

Imaging system 10 may be used for imaging a low intensity fluorescent probe such as fluorescent molecules in a mouse and the like. The low intensity fluorescent probe may be included in any of a variety of living or non-living light-emitting samples. Non-living light-emitting samples may include calibration devices and phantom devices. Living light-emitting samples may include, for example, animals or plants containing light-emitting molecules, tissue culture plates containing living organisms, and multi-well plates (including 96, 384 and 864 well plates) containing living organisms. Animals may include any mammal, such as a mouse or rat containing luciferase-expressing cells.

System 10 finds wide use in imaging and research. The ability to track light-emitting cells in a small laboratory animal such as a mouse or rat opens up a wide range of applications in pharmaceutical and toxilogical research. These include in vivo monitoring of infectious diseases, tumor growth in metastases, transgene expression, compound toxicity, and viral infection or delivery systems for gene therapy. The ability to detect signals in real-time and in living animals means that the progression of a disease or biological process can be studied throughout an experiment with the same set of animals without a need to sacrifice for each data point.

Imaging system 10 comprises an imaging box 12 having a door 18 and inner walls 19 (FIG. 12B) that define an interior cavity 21 that is adapted to receive a mouse 2 in which low intensity light is to be detected. Imaging box 12 is suitable for imaging including the capture of low intensity light on the order of individual photons, for example. Imaging box 12 is often referred to as "light-tight". That is, box 12 seals out essentially all of the external light from the ambient room from entering the box 12, and may include one or more seals that prevent light passage into the box when door 18 is closed. In a specific embodiment, door 18 comprises one or more light-tight features such as a double baffle seal, while the remainder of chamber 21 is configured to minimize any penetration of light into cavity 21.

Mouse 2 is placed within box 12 for imaging by opening door 18, inserting the mouse in chamber 21, and closing door 18. Suitable imaging systems are available from Xenogen Corporation from Alameda, Calif., and include the IVIS® Spectrum, IVIS® 3D Series, IVIS® 200 Series, IVIS® 100 Series, and IVIS® Lumina. Further description of a suitable imaging box 12 is provided in commonly owned U.S. Pat. No. 7,113,217 entitled "3-D Imaging Apparatus for In-Vivo Representations", which is incorporated by reference herein in its entirety for all purposes. Although imaging system 10 is shown with a single cabinet design, other embodiments of the present invention include a disparate imaging box 12 and desktop computer that includes processing system 28 and a dedicated display.

Imaging box 12 includes an upper housing 16 adapted to receive a camera 20 (FIG. 12B). A high sensitivity camera 20, e.g., an intensified or a charge-coupled device (CCD) camera, is mounted on top of upper housing 16 and positioned above imaging box 12. CCD camera 20 is capable of capturing luminescent, fluorescent, structured light and photographic (i.e., reflection based images) images of a living sample or phantom device placed within imaging box 12. One suitable camera includes a Spectral Instruments 620 Series as provided by Spectral Instruments of Tucson, Ariz. CCD camera 20 is cooled by a suitable source thermoelectric chiller to below −90° C. to minimize dark current and any associated noise. Other methods, such as liquid nitrogen, may be used to cool camera 20. Camera may also be side-mounted, or attached to a moving chassis that moves the camera in cavity 21. In a specific embodiment, CCD captures images in the range of about 400 to about 950 nanometers and thus covers the entire visible (VIS) and Near Infrared (NIR) range of interest of optical imaging. In a specific embodiment, camera 20 has a minimum detectable radiance less than 70 photons/sec/cm$^2$/sr.

Imaging system 10 may also comprise a lens (not shown) that collects light from the specimen or phantom device and provides the light to the camera 20. A stage 25 forms the bottom floor of imaging chamber 21 and includes motors and controls that allow stage 25 to move up and down to vary the field of view 23 for camera 20. A multiple position filter wheel may also be provided to enable spectral imaging capability. Imaging box 12 may also include one or more light emitting diodes on the top portion of chamber 21 to illuminate a sample during photographic image capture. Other features may include a gas anesthesia system to keep the mouse anesthetized and/or a heated shelf to maintain an animal's body temperature during image capture and anesthesia.

Imaging box 12 also includes one or more fluorescent excitation light sources. In one embodiment, box 12 includes a trans-illumination device and an epi-illumination device. As mentioned above with respect to FIGS. 6A and 6B, the trans-illumination device is configured to direct light into a first surface of the mouse, where diffused light exits a second surface of the mouse. The epi-illumination device is configured direct light onto a third surface of the specimen, where the diffused light exits the third surface of the mouse. Further description of fluorescent excitation light sources is provided in commonly owned and co-pending patent application Ser. No. 11/434,606, which is incorporated by reference in its entirety for all purposes.

A structured light source is included in imaging box. The structured light source includes a mechanism for transmitting a set of lines onto the object from an angle. The lines are displaced, or phase shifted relative to a stage, when they encounter an object with finite height, such as a mouse. This phase shift provides structured light information for the object. Camera 20 then captures the structured light information. Using software that employs a structured light analysis, surface topography data for the object (over its entire surface or a portion) is determined from the phase shift of the lines.

FIG. 12B shows system 10 with the removal of a side panel for imaging box 12 to illustrate various electronics and processing components included in system 10. Imaging system 10 comprises image processing unit 26 and processing system 28. Image processing unit 26 optionally interfaces between camera 20 and processing system 28 and may assist with image data collection and video data processing. Processing system 28, which may be of any suitable type, comprises hardware including a processor 28a and one or more memory components such as random-access memory (RAM) 28b and read-only memory (ROM) 28c.

Processor 28a (also referred to as a central processing unit, or CPU) couples to storage devices including memory 28b and 28c. ROM 28c serves to transfer data and instructions uni-directionally to the CPU, while RAM 28b typically transfers data and instructions in a bi-directional manner. A fixed disk is also coupled bi-directionally to processor 28a; it provides additional data storage capacity and may also include any of the computer-readable media described below. The fixed disk may be used to store software, programs, imaging data and the like and is typically a secondary storage medium (such as a hard disk).

Processor 28a communicates with various components in imaging box 12. To provide communication with, and control of, one or more system 10 components, processing system 28 employs software stored in memory 28c that is configured to permit communication with and/or control of components in imaging box 12. For example, processing system 28 may include hardware and software configured to control camera 20. The processing hardware and software may include an I/O card, control logic for controlling camera 20. Components controlled by computer 28 may also include motors responsible for camera 20 focus, motors responsible for position control of a platform supporting the sample, a motor responsible for position control of a filter lens, f-stop, etc.

Processing system 28 may also interface with an external visual display (such as computer monitor) and input devices such as a keyboard and mouse. A graphical user interface that facilitates user interaction with imaging system 10 may also be stored on system 28, output on the visual display and receive user input from the keyboard and mouse. The graphical user interface allows a user to view imaging results and also acts an interface to control the imaging system 10. One suitable imaging software includes "LivingImage" as provided by Xenogen Corporation of Alameda, Calif.

Processing system 28 may comprise software, hardware or a combination thereof. System 28 may also include additional imaging hardware and software, tomographic reconstruction software that implements process flows and methods described above, and image processing logic and instructions for processing information obtained by camera 20.

In one embodiment, imaging system 10 includes a spectral unmixing software tool. The spectral unmixing tool measures one or more images at multiple wavelengths and separates image data according to contributing spectra in the image in an effort to separate the fluorescence spectra of interest. The spectral unmixing tool may be considered an analysis tool for multi-spectral images that unmixes spectral components and finds each of their respective spectrums and spatial distribution maps. In a specific embodiment, a user initiates the spectral unmixing tool and software with an appropriate user interface command. In another specific embodiment, spectral unmixing techniques described herein are automated, transparent to a user, and occur whenever a tomographic assessment is performed without input from a user. In another specific embodiment, the spectral unmixing tool is programmed with a learning ability. In this case, the spectral unmixing tool saves the spectra unmixed from one experiment or data set and uses it in a latter experiment or data processing.

Regardless of the imaging and computing system configuration, imaging apparatus 10 may employ one or more memories or memory modules configured to store program instructions for spectral unmixing and other functions described herein. Such memory or memories may also be configured to store data structures, imaging data, or other specific non-program information described herein. Because such information and program instructions may be employed to implement the systems/methods described herein, the present invention relates to machine-readable media that include program instructions, state information, etc. for performing various operations described herein. Examples of tangible machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter. The invention may also be embodied in a carrier wave traveling over an appropriate medium such as airwaves, optical lines, electric lines, etc.

In a specific embodiment, the spectral unmixing method 66 of FIG. 5 was implemented in C++, and included interfaces for creating and accepting data, controls and constraints. Other programming languages are suitable for use, as one of skill in the art will appreciate.

Spectral unmixing as described herein finds use in a wide array of imaging and research applications such as oncology, infectious disease research, gene expression research, and toxicology, for example. The spectral unmixing techniques described herein place no restrictions on the source distribution, such as the number of probes in the sample or the sizes and shapes of the sources, and no restrictions on the geometry, size or shape of the surface.

In addition, although the present invention has been described with respect to a fluorescent probe that emits light, spectral unmixing techniques described herein may be used on any type of internal light source, including one or more bioluminescent sources.

While this invention has been described in terms of several preferred embodiments, there are alterations, permutations, and equivalents which fall within the scope of this invention which have been omitted for brevity's sake. For example, although the methods have primarily been discussed with respect to fluorescent light imaging, the present invention is also well-suited for use with other wavelength ranges and imaging modalities, such as near IR. In addition, although the methods have been described with respect to solving for autofluorescence separately from the tomographic reconstruction to expedite finding a solution, they may be combined to accommodate minor changes in tissue properties, albeit with less constrained computations and a need for more computational resources. It is therefore intended that the scope of the invention should be determined with reference to the appended claims.

What is claimed is:

1. A method for spectrally unmixing light data corresponding to light emitted from multiple light sources internal to an animal, the method comprising:

selecting an excitation wavelength band for excitation light provided to the animal;

selecting an emission wavelength band that limits light wavelengths collected from the animal;

providing excitation light, into the animal, that is limited to the excitation wavelength band;

capturing a first image of at least a portion of the animal, where the first image includes light data that is limited in wavelength to the emission wavelength band and corresponds to light emitted by multiple fluorescent light sources internal to the animal;

changing the excitation wavelength band and/or the emission wavelength band;

capturing at least one additional image of at least the portion of the animal that uses a different combination of excitation wavelength band and emission wavelength band for each additional image, where each additional image includes light data that corresponds to light emitted by the multiple fluorescent light sources internal to the animal and is limited in wavelength to the emission wavelength band of the different combination; and unmixing spectra for the multiple fluorescent light sources derived from the first image limited in wavelength to the emission wavelength band and the at least one additional image limited in wavelength to the emission wavelength band to determine a pure spectrum for each light source in the animal using an iterative solution process by a processor, wherein said iterative solution process by the processor includes applying both a unimodality constraint that limits the pure spectrum for each light source in the process to having a single peak, and a bandpass constraint that limits the pure spectrum for each light source in the process to within a desired wavelength range.

2. The method of claim 1 further comprising determining the number of fluorescent light sources before unmixing spectra for the multiple fluorescent light sources.

3. The method of claim 1 wherein a total number of images captured by the camera is no less than the number of fluorescent light sources in the animal.

4. The method of claim 1 wherein the different combination for each additional image uses a common excitation wavelength band and multiple emission wavelength bands.

5. The method of claim 1 wherein the different combination for each additional image uses a common emission wavelength band and multiple excitation wavelength bands.

6. The method of claim 1 where the excitation light is provided into the animal from a portion of the animal that is visible to the camera during image capture.

7. The method of claim 1 where the excitation light is provided into the animal from a portion of the animal that is not visible to the camera during image capture.

8. The method of claim 1 wherein the iterative solution process also outputs a spatial distribution map for each of the multiple fluorescent light sources internal to the animal, where each spatial distribution map provides a two dimensional representation of a distribution of a fluorescent light source in the animal.

9. The method of claim 1 further comprising providing an initial estimate of each pure spectrum for the multiple fluorescent light sources.

10. The method of claim 1 wherein the constraint further includes a non-negativity constraint that limits the spectrum for each light source to a non-negative number.

11. The method of claim 1 further comprising applying a spatial distribution map constraint during the iterative solution process.

12. The method of claim 11 wherein the spatial distribution map constraint includes a region of interest constraint that limits a spatial area for a fluorescent light source in a spatial distribution map produced by the iterative solution process.

13. The method of claim 1 wherein the multiple fluorescent light sources include tissue autofluoresence in the animal.

14. The method of claim 1 wherein the first image and the one or more additional images are captured in a light tight imaging box and the animal emits light in the range of about $10^4$ to about $10^{14}$ photons/second.

15. Logic that is encoded in one or more tangible and non-transitory media for execution by a processor and, when executed, is operable to spectrally unmix spectra corresponding to light emission from multiple light sources internal to an animal, the logic including:
  instructions for selecting an excitation wavelength band for excitation light provided to the animal;
  instructions for selecting an emission wavelength band that limits light wavelengths collected from the animal;
  instructions for providing excitation light, into the animal, that is limited to the excitation wavelength band;
  instructions for capturing a first image of at least a portion of the animal, where the first image includes light data that is limited in wavelength to the emission wavelength band and corresponds to light emitted by multiple fluorescent light sources internal to the animal;
  instructions for changing the excitation wavelength band and/or the emission wavelength band;
  instructions for capturing one or more additional images of at least the portion of the animal, using a different combination of excitation wavelength band and emission wavelength band for each additional image, where each additional image includes light data that corresponds to light emitted by the multiple fluorescent light sources internal to the animal and is limited in wavelength to the emission wavelength band of the different combination; and
  instructions for unmixing spectra for the multiple fluorescent light sources derived from the first image limited in wavelength to the emission wavelength band and the at least one additional image limited in wavelength to the emission wavelength band to determine a pure spectrum for each light source in the animal using an iterative solution process,
  wherein said iterative solution process includes applying both a unimodality constraint that limits the pure spectrum for each light source in the process to having a single peak, and a bandpass constraint that limits the pure spectrum for each light source in the process to within a desired wavelength range.

16. A method for obtaining a three dimensional representation of a light source distribution located inside an animal, the method comprising:
  selecting an excitation wavelength band for excitation light provided to the animal;
  selecting an emission wavelength band that limits light wavelengths collected from the animal;
  providing excitation light, into the animal, that is limited to the excitation wavelength band;
  capturing a first image of at least a portion of the animal, where the first image includes light data that is limited in wavelength to the emission wavelength band and corresponds to light emitted by multiple fluorescent light sources internal to the animal;
  changing the excitation wavelength band and/or the emission wavelength band;
  capturing one or more additional images of at least the portion of the animal, using a different combination of excitation wavelength band and emission wavelength band for each additional image, wherein each additional image includes light data that corresponds to light emitted by the multiple fluorescent light sources internal to the animal and is limited in wavelength to the emission wavelength band of the different combination;
  using an iterative solution process by a processor, unmixing spectra for the multiple fluorescent light sources derived from the first image limited in wavelength to the emission band and the at least one additional image limited in wavelength to the emission band to provide a pure spectrum and spatial distribution map for one of the multiple fluorescent light sources;
  obtaining a three dimensional representation of a surface portion of the animal;
  combining the spatial distribution map and the three dimensional representation of the surface portion of the animal to generate a three-dimensional distribution of light emission from the surface portion of the animal corresponding to the one fluorescent light source; and
  determining a three-dimensional representation of a distribution of the one fluorescent light source internal to the animal using the three-dimensional distribution of light emission from the surface portion of the animal corresponding to the one fluorescent light source.

17. The method of claim 16 wherein the fluorescent excitation light is incident in an epi-illumination mode or a trans-illumination mode.

18. The method of claim 16 wherein using the iterative solution process comprises applying both a unimodality constraint that limits the pure spectrum for the one fluorescent light source to having a single peak, and a bandpass constraint that limits the pure spectrum for the one fluorescent light source to within a desired wavelength range.

19. The method of claim 18 wherein among the first and one or more additional images, a first image corresponds to a first position of an excitation light source relative to the animal, and a second image corresponds to a second position of the excitation light source relative to the animal that is different from the first position.

20. The method of claim 19 wherein the first position of the excitation light source corresponds to a first trans-illumination position and the second position of the excitation light source corresponds to a second trans-illumination position.

21. A method for spectrally unmixing light data corresponding to light emitted from multiple light sources internal to an animal, the method comprising:
  selecting an emission wavelength band that limits light wavelengths collected from the animal;
  capturing a first image of at least a portion of the animal, where the first image includes light data that is limited in wavelength to the emission wavelength band and corresponds to light emitted by the multiple light sources internal to the animal;
  changing the emission wavelength band;
  capturing one or more additional images of at least the portion of the animal, using a different emission wavelength band for each additional image, where each additional image includes light data that corresponds to light emitted by the multiple light sources internal to the animal and is limited in wavelength to the different emission wavelength band; and using an iterative solution process by a processor, unmixing spectra for the multiple light sources derived from the first image limited in wavelength to the emission wavelength band and the at least one additional image limited in wavelength to the emission wavelength band to determine a pure spectrum for each light source in the animal, wherein the iterative solution process implements a multivariate curve resolution and iteratively solves for the pure spectrum of each of the multiple light sources using finishing criteria; and wherein said iterative solution process by the processor includes applying both a unimodality constraint that limits the pure spectrum for each light source in the process to having a single peak, and a bandpass constraint that limits the pure spectrum for each light source in the process to within a desired wavelength range.

22. The method of claim 21 wherein the multiple light sources include a bioluminscent light source and tissue autofluoresence in the animal.

23. The method of claim 21 further comprising selecting an excitation spectrum for excitation light provided to the animal and providing excitation light, into the animal, that is limited to the excitation wavelength band, when the multiple light sources include a fluorescent light source.

24. The method of claim 23 wherein the iterative solution process operates simultaneously on images for a) multiple illumination positions, b) multiple combinations of excitation wavelength bands, and c) multiple emission wavelength bands.

25. The method of claim 21 wherein the iterative solution process also outputs a spatial distribution map for each of the multiple light sources internal to the animal, where each spatial distribution map provides a two dimensional representation of a distribution of one of the multiple light sources in the animal.

26. The method of claim 21 wherein the finishing criteria uses an alternating least square method.

27. An imaging system for imaging an animal, the imaging system comprising:
    an imaging chamber that includes
        a set of walls and a door that enclose an interior cavity,
        a stage configured to support the animal within the interior cavity,
        a camera, and
        a fluorescent excitation source; and
    a processing system including a processor and memory, the memory including:
        instructions for selecting an excitation wavelength band for excitation light provided to the animal,
        instructions for selecting an emission wavelength band that limits light spectra collected from the animal,
        instructions for obtaining one or more fluorescent images using the camera, and
        instructions for unmixing spectra for the multiple fluorescent light sources derived from the one or more fluorescent images to determine a pure spectrum for each fluorescent light source using an iterative solution process,
        wherein said iterative solution process comprises applying a unimodality constraint that limits the pure spectrum for each light source to having a single peak, and a bandpass constraint that limits the pure spectrum for each light source to within a desired wavelength range.

28. The imaging system of claim 27 further comprising:
    an excitation filter configured to intercept excitation light produced by the fluorescent excitation source before the excitation light reaches the animal; and
    an emission filter configured to intercept emission light emitted from the animal before the emission light reaches the camera.

29. The imaging system of claim 27 further comprising a structured light projector.

30. The imaging system of claim 27 wherein the interior cavity is substantially light tight.

31. The imaging system of claim 27 wherein the fluorescent excitation source is below the stage.

* * * * *

UNITED STATES PATENT AND TRADEMARK OFFICE
CERTIFICATE OF CORRECTION

PATENT NO. : 10,335,038 B2
APPLICATION NO. : 11/844920
DATED : July 2, 2019
INVENTOR(S) : Heng Xu and Bradley W. Rice Page 1 of 1

It is certified that error appears in the above-identified patent and that said Letters Patent is hereby corrected as shown below:

In the Specification

Column 1
Line 6 (Approx.), after "U.S.C." insert -- § --

In the Claims

Column 23
Line 10, in Claim 13, delete "autofluoresence" and insert -- autofluorescence --

Column 25
Line 23, in Claim 22, delete "bioluminscent" and insert -- bioluminescent --
Line 24, in Claim 22, delete "autofluoresence" and insert -- autofluorescence --

Signed and Sealed this
Seventeenth Day of September, 2019

Andrei Iancu
*Director of the United States Patent and Trademark Office*